(12) United States Patent
Puerta et al.

(10) Patent No.: US 8,008,510 B2
(45) Date of Patent: Aug. 30, 2011

(54) METALLOPROTEIN INHIBITORS

(75) Inventors: David T. Puerta, Melrose, MA (US);
Seth M. Cohen, San Marcos, CA (US);
Jana A. Lewis, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/722,623

(22) Filed: Mar. 12, 2010

(65) Prior Publication Data

US 2010/0173952 A1 Jul. 8, 2010

Related U.S. Application Data

(60) Division of application No. 11/568,505, filed as application No. PCT/US2005/014747 on Apr. 28, 2005, now Pat. No. 7,705,164, and a continuation-in-part of application No. PCT/US2005/009277, filed on Mar. 21, 2005.

(60) Provisional application No. 60/566,882, filed on Apr. 29, 2004, provisional application No. 60/576,444, filed on Jun. 3, 2004.

(51) Int. Cl.
*C07D 213/63* (2006.01)
*C07D 315/00* (2006.01)

(52) U.S. Cl. ...................... 549/291; 549/418
(58) Field of Classification Search .............. 546/291
See application file for complete search history.

(56) References Cited

U.S. PATENT DOCUMENTS

| | | | |
|---|---|---|---|
| 4,585,780 A | 4/1986 | Hider et al. | |
| 5,981,496 A | 11/1999 | Cohen et al. | |
| 6,552,073 B1 | 4/2003 | Leblanc et al. | |
| 6,825,204 B2 | 11/2004 | Liu | |
| 6,932,960 B2 | 8/2005 | Liu | |
| 7,579,486 B2 | 8/2009 | Puerta et al. | |
| 7,705,164 B2 | 4/2010 | Puerta et al. | |
| 7,786,316 B2 | 8/2010 | Puerta et al. | |
| 2004/0063673 A1 | 4/2004 | Johnson | |
| 2007/0117848 A1 | 5/2007 | Puerta et al. | |
| 2008/0103129 A1 | 5/2008 | Zhang et al. | |
| 2008/0161362 A1 | 7/2008 | Puerta et al. | |
| 2009/0286987 A1 | 11/2009 | Puerta et al. | |

FOREIGN PATENT DOCUMENTS

| | | |
|---|---|---|
| EP | 1006112 A1 | 6/2000 |
| WO | WO-2004/110442 A1 | 12/2004 |
| WO | WO-2005/110399 A2 | 11/2005 |
| WO | WO-2006/028523 A2 | 3/2006 |

OTHER PUBLICATIONS

"U.S. Appl. No. 11/554,475, Preliminary Amendment filed Oct. 22, 2007", 7 pgs.
"U.S. Appl. No. 11/554,475, Response filed Jan. 9, 2009 to Final Office Action mailed Nov. 12, 2008", 17 pgs.
"U.S. Appl. No. 11/554,475, Final Office Action mailed Feb. 4, 2009", 7 pgs.
"U.S. Appl. No. 11/554,475, Advisory Action mailed May 15, 2009", 3 pgs.
"U.S. Appl. No. 11/554,475, Final Office Action mailed Nov. 12, 2008", 11 pgs.
"U.S. Appl. No. 11/554,475, Interview Summary of Jun. 3, 2008", 1 pg.
"U.S. Appl. No. 11/554,475, Non-Final Office Action mailed Jun. 19, 2008", 10 pgs.
"U.S. Appl. No. 11/554,475, Notice of Allowance mailed Jun. 3, 2009", 6 pgs.
"U.S. Appl. No. 11/554,475, Response filed Apr. 21, 2009 to Final Office Action mailed Feb. 4, 2009", 10 pgs.
"U.S. Appl. No. 11/554,475, Response filed Apr. 18, 2008 to Restriction Requirement mailed Feb. 26, 2008", 10 pgs.
"U.S. Appl. No. 11/554,475, Restriction Requirement mailed Feb. 26, 2008", 8 pgs.
"U.S. Appl. No. 11/554,475, Summary of Interview Under 37 C.F.R. § 1,133(b) filed Jul. 9, 2008", 1 pg.
"U.S. Appl. No. 11/554,475, Amendment and Response filed Sep. 17, 2008 to Non-Final Office Action mailed Jun. 19, 2008", 11 pgs.
"U.S. Appl. No. 11/568,505, Preliminary Amendment mailed Oct. 30, 2006", 11 pgs.
"U.S. Appl. No. 11/568,505, Supplemental Preliminary Amendment filed Oct. 26, 2007", 9 pgs.
"U.S. Appl. No. 11/568,505, Second Preliminary Amendment filed Aug. 20, 2007", 10 pgs.
"U.S. Appl. No. 11/568,505, Notice of Allowance Mailed Dec. 7, 2009", 6 pgs.

(Continued)

*Primary Examiner* — Nizal Chandrakumar
(74) *Attorney, Agent, or Firm* — Schwegman, Lundberg & Woessner, P.A.

(57) ABSTRACT

The present invention relates to metalloprotein inhibitors comprising:
 a. an organic substituent and at least one zinc binding group (ZBG) covalently attached thereto; or
 b. a ZBG substituted by a side chain wherein the ZBG is of formula (I):

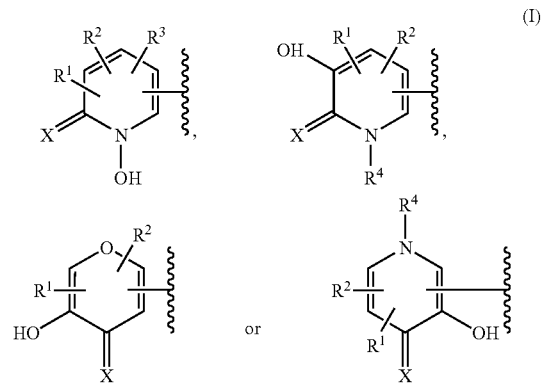

wherein X is O or S and each $R^1$, $R^2$, $R^3$, and $R^4$ is individually hydrogen or an organic radical. The metalloprotein inhibitors are useful for preventing or treating a pathological disease, condition, or symptom that is associated with pathological metalloprotein activity and/or that is alleviated by inhibition of said activity.

6 Claims, 6 Drawing Sheets

OTHER PUBLICATIONS

"U.S. Appl. No. 11/568,505, Final Office Action mailed Oct. 21, 2009", 8 pgs.

"U.S. Appl. No. 11/568,505, Non-Final Office Action mailed Nov. 3, 2008", 12 pgs.

"U.S. Appl. No. 11/568,505, Non-Final Office Action mailed Feb. 25, 2009", 16 pgs.

"U.S. Appl. No. 11/568,505, Response filed Jul. 23, 2009 to Non Final Office Action mailed Feb. 25, 2009", 26 pgs.

"U.S. Appl. No. 11/568,505, Response filed Oct. 17, 2008 to Restriction Requirement mailed Jun. 19, 2008", 15 pgs.

"U.S. Appl. No. 11/568,505, Response filed Nov. 6, 2009 to Final Office Action mailed Oct. 21, 2009", 12 pgs.

"U.S. Appl. No. 11/568,505, Response filed Feb. 2, 2009 to Non-Final Office Action mailed Nov. 3, 2008", 21 pgs.

"U.S. Appl. No. 11/568,505, Restriction Requirement mailed Jun. 19, 2008", 7 pgs.

"U.S. Appl. No. 12/503,190, Non-Final Office Action mailed Jan. 12, 2010", 4 pgs.

"U.S. Appl. No. 12/503,190, Preliminary Amendment filed Nov. 19, 2009", 5 pgs.

"U.S. Appl. No. 12/503,190, Response filed Feb. 11, 2010 to Non Final Office Action mailed Jan. 12, 2010", 7 pgs.

"European Applicatiion Serial No. 05818191.8, Communication Pursuant to Article 96(2)EPC mailed Jul. 5, 2007", 4 pgs.

"European Applicatiion Serial No. 05818191.8, Response filed Nov. 7, 2007 to Communication mailed Jul. 5, 2007", 20 pgs.

"European Application Serial No. 05818191.8, Communication mailed Aug. 7, 2009", 4 pgs.

"European Application Serial No. 05818191.8, Response filed Jan. 22, 2010 to Communication mailed Aug. 7, 2009", 8 pgs.

"International Application Serical No. PCT/US2005/014747, International Search Report mailed Mar. 10, 2006", 6 pgs.

"International Application Serial No. PCT/US2005/014747, Written Opinion mailed Mar. 10, 2006", 6 pgs.

Atkinson, J. G., et al., "Kojic Amine—A Novel γ-Aminobutyric Acid Analogue", *Journal of Medicinal Chemistry*, 22 (1), (1979), 99-106.

Aytemir, M. D., et al., "Synthesis and Evaluation of Antimicrobial Activity of New 3-Hydroxy-6-methyl-4-xox-4H-pyran-2-carboxamide Derivatives", *Turkish Journal of Chemistry*, 27(6), (2003), 757-764.

Aytemir, M. D., et al., "Synthesis of New Antimicrobial Agents; Amide Derivatives of Pyranones and Pyridinones", *Turk. J. Chem.*, 27, (2003), 445-452.

Beckett, R. P., et al., "Matrix Metalloproteinase Inhibitors 1998", *Expert Opinion on Therapeutic Patents*, 8(3), (Mar. 1998), 259-282.

Beckett, R. P., et al., "Recent Advances in Matrix Metalloproteinase Inhibitor Research", *Drug Discovery Today*, 1(1), (Jan. 1996), 16-26.

Belonosov, I. S., et al., "4—Pyronecarboxylic acids and their transformations", *Zhumai Prikladnoi Khimii*( Sankt-Petersburg, Russian Federation), vol. 24, (Abstract Only), (1951), 1 pg.

Brinckerhoff, C. E., et al., "Matrix Metalloproteinases: A Tail of a Frog That Become a Prince", *Nature Reviews—Molecular Cell Biology*, 3, (Mar. 2002), 207-214.

Chen, L., et al., "Crystal Structure of the Stromelysin Catalytic Doman at 2.0 A Resolution: Inhibitor-Induced Conformational Changes", *Journal of Molecular Biology*, 293, (1999), 545-557.

Cohen, S. M., et al., "Mixed Hydroxypyridinonate Ligands as Iron Chelators", *American Chemical Society*, 39, (Aug. 30, 2000), 4339-4346.

Cohen, S. M., et al., "Syntheses and Relaxation Properties of Mixed Gadolinium Hydroxypyridinonate MRI Contrast Agents", *American Chemical Society*, 39, (2000), 5747-5756.

Cohen, S. M., et al., "Synthesis and Metal Binding Properties of Salicylate-, Catecholate-, and Hydroxypyridinonate-Functionalized Dendrimers", *Chem. Eur. J.*, 7(1), 2001, 272-279.

Dilsiz, A. M., et al., "Synthesis and Evaluation of Antimicrobial Activity of New 3-Hydroxy-6-methyl-4-oxo-4H-pyran-2-carboxamide Derivatives", *Turkish Journal of Chemistry*, 27 (6), (2003), 757-764.

Georg Iou, N. A., et al., "Human Immunodeficiency Virus Type 1 Replication Inhibiton by the Bidentate Iron Chelators CP502 and CP511 IS Caused by Proliferation Inhibition and the Onset of Apoptosis", *European Journal of Clinical Investigation*, 32((Issue S1), (2002), 91-96.

Gorden, A. E. V., et al., "Rational Design of Sequestering Agents for Plutonium and Other Actinides", *Chemical Reviews*, 103(11), (2003), 4207-4282.

Hajduk, P. J., et al., "NMR-Based Modification of Matrix Metalloproteinase Inhibitors With Improved Bioavailability", *Journal of Medicinal Chemistry*, 45, (2002), 5628-5639.

Hoeksema, H., et al., "The chemistry of rubradirin. III. The rubradiric acids and the structure of rubradirin", *Journal of Antibiotics*, 32.(7), (Abstract Only), (1979), 1 pg.

Hoeksema, H., et al., "The chemistry of rubradirin. III. The rubradiric acids and the structure of rubradirin," *Journal of Antibiotics*, 32(7), (1979), 773-776.

Jacobsen, F. E., et al., "Using Model Complexes to Augment and Advance Metalloproteinase Inhibitor Design", *Inorganic Chemistry*, 43, (2004), 3038-3047.

Lewis, J. A., et al., "Metal Complexes of the trans-Influencing Ligand Thiomaltol", *Inorganic Chemistry*, 42(23), (2003), 7455-7459.

Lim, S., et al., "Competitive Inhibition of Tyrosinase by 5-Hydroxy-2-phenylalanylaminomethyl-4-pyron", *Yakhak Hoechi*, 44(3), (2000), 279-282.

Liu, Z. D., et al., "Design of iron chelators with therapeutic application", *Coordination Chemistry Reviews*, 232, (2002), 151-171.

Liu, Z. D., et al., "Design, Synthesis, and Evaluation of Novel 2-Substituted 3-Hydroxypyridin-4-ones: Structure—Activity Investigation of Metalloenzyme Inhibition by Iron Chelators", *Journal of Medicial Chemistry*, 45(3), (2002), 631-639.

Liu, Z. D., et al., "Synthesis of 2-Amido-3-hydroxypryidin-4(1H)-ones: Novel Iron Chelators with Enhanced pFe $^{3+}$Values", *Bioorganic and Medicinal Chemistry*, 9(3), (2001), 563-573.

Opdenakker, G., et al., "Cytokines and Proteases in Invasive Processes: Molecular Similarities Between Inflammation and Cancer", *Cytokine*, 4(4), (Jul. 1992), 251-258.

Overall, C. M., et al., "Strategies for NMP Inhibition in Cancer: Innovations for the Post-Trial Era", *Nature Reviews, Cancer*, 2, (Sep. 2002), 657-672.

Pace, P., et al., "The monoethyl ester of meconic acid is an active site inhibitor of HCV NS5B RNA-dependent RNA polymerase", *Bioorganic & Medicinal Chemistry Letters*, 14, (2004), 3257-3261.

Piyamongkol, S., et al., "Novel synthetic approach to 2-(1'-hydroxyalkyl)- and 2-amido-3-hydroxypyridin-4-ones", *Tetrahedron*, 57, (2001), 3479-3486.

Puerta, D. T., et al., "A Bioinorganic Perspective on Matrix Metaloproteinase Inhibition", *Current Topics in Medicinal Chemistry*, 4, (2004), 1551-1573.

Puerta, D. T., et al., "Elucidating Drug-Metalloprotein Interactions with Tris(pyrazolyl)borate Model Complexes", *Inorganic Chemistry*, 41(20), (2002), 5075-5082.

Puerta, D. T., et al., "Examination of Novel Zinc-Binding Groups for Use in Matrix Metalloproteinase Inhibitors", *Inorganic Chemistry*, 42, 2003, 3423-3430.

Puerta, D. T., et al., "From Model Complexes to Metalloprotein Inhibition: A Synergistic Approach to Structure-Based Drug Discovery", *Angewandte Chemie International Edition*, 42(32), (2003), 3772-3774.

Puerta, D. T., et al., "New Beginnings for Matrix Metalloproteinase Inhibitors: Identification of High-Affinity Zinc-Binding Groups", *Journal of the American Chemical Society*, 126(27), (2004), 8388-8389.

Puerta, D. T, et al., "Potent, Selective Pyrone-Based Inhibitors of Stromelysin-l", *J. Am. Chem. Soc.*, 127(41), (2005), 14148-14149.

Scarrow, R. C., et al., "Ferric Ion Sequestering Agents", *Inorganic Chemistry*, 24(6), (1984), 954-967.

Shapiro, S. D., et al., "Proteolysis In The Lungs", *Eur Respir J*, 22 (Suppl. 44), (2003), 30s-32s.

Skiles, J. W., et al., "The Design, Structure, and Therapeutic Application of Matrix Metalloproteinase Inhibitors", *Current Medicinal Chemistry*, 8(4), (2001), 425-474.

Storr, T., et al., "Vanadyl-Thiazolidinedione Combination Agents for Diabetes Therapy", *Bioconjugate Chem.* 14 (1), (2003), 212-221.

White, D. L., et al., "Specific Sequestering Agents for the Actinides. 16. Syntheses and Initial Biological Testing of Polydentate Oxohydroxypyridinecarboxylate Ligands", *J. Med. Chem.*, 31, (1988), 11-18.

Whittaker, M., et al., "Design and Therapeutic Application of Matrix Metalloproteinase Inhibitors", *Chem. Rev.* 99, (1999), 2735-2776.

Whittaker, M., et al., "Matrix Metalloproteinases and Their Inhibitors—Current Status and Future Challenges", *Celltransmissions*, 17(1), (2001), 3-14.

Wojtowicz-Praga, S. M., et al., "Matrix Metalloproteinase Inhibitors", *Investigational New Drugs*, 15, (1997), 61-75.

Woods, L. L., "Mannich Bases from Kojic Acid and Aryl Amines", *J. of the American Chemistry Society*, 68, (1946), 2744-2745.

Xu, J., et al., "Specific Sequestering Agents for the Actinides. 28. Syntheses and Initial Evaluation of Multidentate 4-Carbamoyl-3-hydroxy-1-methyl-2(1H)-pyridinone Ligands for in Vivo Plutonium (IV) Chelation", *J. Med. Chem*, 38, (1995), 2606-2614.

Yeh, L.-A., et al., "Inhibition of Metalloproteinase by Futoenone Derivatives", *Biorganic & Medicinal Chemistry Letters*, 5(15), (Aug. 1995), 1637-1642.

"U.S. Appl. No. 11/554,475, Examiner Interview Summary mailed Apr. 15, 2009", 2 pgs.

"U.S. Appl. No. 11/568,505, Examiner Interview Summary mailed Nov. 20, 2009", 3 pgs.

"U.S. Appl. No. 12/503,190, Notice of Allowance mailed Apr. 23, 2010", 6 pgs.

Agrawal, Arpita, et al., "Thioamide Hydroxypyrothiones Supersede Amide Hydroxypyrothiones in Potency against Anthax Lethan Factor", J. Med. Chem. 52, Doi: 10.1021/jm8013212, (2009), 1063-1074.
Agrawal, Arpita, et al., "Zinc-Binding Groups Modulate Selective Inhibition of MMPs", ChemMedChem 3, DOI: 10.1002/cmdc.200700290, (2008), 812-820.
Wischeler, Johannes Schulze, et al., "Bidentate Zinc Chelators for a-Carbonic Anhydrases that Produce a Trigonal Bipyramidal Coordination Geometry", ChemMedChem 5, DOI: 10.1002/cmdc.201000200, (2010), 1609-1615.

| ZBG | MMP-1[a] | MMP-2[a] | MMP-3[a] | MMP3 Colorimetric2[a] |
|---|---|---|---|---|
| AHA | 41600(±400) | 15300(±3000) | 25000(±4000) | |
| 1 | 5960(±40) | 5600(±100) | 1600(±100) | 1500((±10) |
| 2 | 4200(±300) | 2600(±400) | 5100(±200) | |
| 4 | not determined | not determined | 7200(±1200) | 8300(±900) |
| 5 | 4200(±300) | 2600(±100) | 5700(±100) | 16000(±2000) |
| 6 | not determined | not determined | 5700(±200) | 5000(±1000) |
| 7 | 490(±10) | 100(±40) | 35(±3) | 20(±4) |
| 8 | 680(±20) | 380(±10) | 362(±3) | |
| 9 | 150(±10) | 60(±10) | 140(±20) | |
| 10 | not determined | not determined | 120 (±40) | |
| 11 | 400(±10) | 140(±10) | 210 (±20) | |

[a] values based on at least three repetitions

FIG. 4

METALLOPROTEIN INHIBITORS

RELATED APPLICATIONS

This application is a divisional application of U.S. patent application Ser. No.: 11/568,505, filed Aug. 22, 2007, now U.S. Pat. No. 7,705,164, which application is a U.S. National Stage Application under 35 U.S.C. §371 of PCT/US2005/014747 filed Apr. 28, 2005, and published in English as WO 2006/028523 A2 on Mar. 16, 2006 and republished as WO 2006/028523 A3, which claims the benefit under 35 U.S.C. §119(e) of U.S. Provisional Application Serial Nos. 60/566,882 filed Apr. 29, 2004, and of 60/576,444 filed Jun. 3, 2004; PCT/US2005/014747 is also a continuation-in-part of PCT/US2005/009277 filed Mar. 21, 2005 and published in English as WO 2005/110399 A2 on Nov. 24, 2005 and republished as WO 2005/110399 A3, the contents of which applications and publications are incorporated herein by reference in their entireties.

BACKGROUND OF THE INVENTION

Metalloprotein inhibition is important for many potential medicinal and cosmetic applications. MMPs are a class of zinc(II)-containing hydrolytic enzymes involved in the breakdown of the extracellular matrix and the basement-membrane including components such as aggrecan, collagen, elastin, fibronectin, gelatin, and laminin. The ability of MMPs to degrade components of the extracellular matrix is essential to tasks such as cell growth, cell division, bone growth, wound healing, embryogenesis, and angiogenesis.[1,2] Disruption of the regulation of MMP activity is correlated to disease states including but not limited to cardiovascular disease, stroke, arthritis, and tumor metastasis.[1-3] Many factors must be considered in designing an effective and selective drug. In the case of matrix metalloproteinase inhibitors (MMPi), the drug typically consists of two parts, a peptidomimetic backbone and a zinc-binding group (ZBG). The backbone serves as a substrate analogue, allowing the inhibitor to fit in the active-site cleft of the enzyme. The ZBG binds to the catalytic zinc(II) ion, thereby rendering the MMP inactive. The vast majority of MMPi investigations have focused on improving the backbone interactions of MMPi while opting to use a well-known ZBG, namely a hydroxamic acid moiety, that has been in regular use for more than 20 years.[1] Although extensive efforts have been made to improve MMPi by manipulating the substrate-like backbone of the drug, significantly fewer efforts have concentrated on improving the ZBG. Thus, there is a need for the identification of more potent and selective ZBGs to take MMPi toward a more productive second generation of development.

Histone deacetylases (HDACs) and the silent information regulator-like family of NAD-dependent deacetylases are important in transcriptional regulation. Acetylation neutralizes the lysine charge, and DNA unwinds, thus allowing active gene expression to occur.[4] Deacetylation leads to the packing of nucleosomes as chromatins and thus gene repression. HDACs deacetylate using an activated water in the active site where two glutamic acid residues and a histidine residue are coordinated to an active site metal ion with a histidine-aspartate charge-relay system.[5] Anomalous HDAC activity has been associated with cancer, and HDAC inhibitors have been proposed as cancer treatments.[6] With HDAC inhibitors (HDACi), the drug generally has a form of a ZBG to bind the catalytic zinc ion, a linker to interact with the narrow channel leading down to the active site, and a surface recognition or capping group that will interact with the surface of the protein.[7] Some of the HDACi in the literature include short chain fatty acids like valproic acid, hydroxamates like trichostatin A, cyclic hydroxamic-acid-containing peptide compounds, epoxides, and benzamidines.[7,8]

Anthrax spores are taken up by alveolar macrophages and germinate in the lymphnodes where the spores create toxins to inhibit immune responses.[9] Anthrax is often asymptomatic until it reaches the blood, and then it is often fatal and non-responsive to traditional antibiotics. In order for an anthrax infection to be toxic, the protective antigen (PA) must form a heptamer that will mediate entry of up to three molecules of edema factor (EF) and lethal factor (LF) per heptamer into cells.[10] Anthrax lethal factor is one of three proteins involved in anthrax pathogenesis and lethality. Inactivation of the LF gene in B. anthracis leads to a thousand-fold or greater reduction of virulence, which suggests that anthrax pathology is largely determined by LF.[11] LF cleaves the N-terminus of the D-domain of mitogen-activated protein kinase kinases (MAPKK), which impairs essential signal transduction pathways such as inhibiting the activation of p38 MAPK switching the signaling macrophage apoptosis before macrophages can be activated and spread the alarm of infection.[9] The active site of anthrax lethal factor consists of two histidine residues and a glutamic acid residue bound to a zinc(II) ion. Again, many known LF inhibitors contain a hydroxamate as a ZBG, and some proposed inhibitors are based on animoglycosides, small peptides attached to a ZBG, or were identified from the NCI Diversity Set.[12-14]

SUMMARY OF THE INVENTION

The present invention provides metalloprotein inhibitors (MPI), such as matrix metalloproteinase inhibitors (MMPi), histone deacetylase inhibitors (HDACi), or anthrax lethal factor inhibitors (LFi).

The present invention provides a metalloprotein inhibitor, of formula (I):

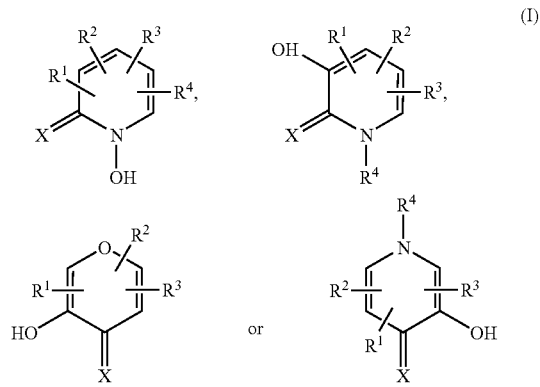

wherein X is O or S and each $R^1$, $R^2$, $R^3$, and $R^4$ is individually hydrogen or another substituent, wherein at least one of $R^1$, $R^2$, $R^3$ and $R^4$ is an organic substituent, or a pharmaceutically acceptable salt thereof. Preferably, at least two of $R^1$, $R^2$, $R^3$ and $R^4$ is an organic substituent.

In another embodiment, the present invention provides a metalloprotein inhibitor comprising: an organic substituent and two or more zinc binding groups (ZBG) covalently attached thereto, wherein the ZBG is of formula (II):

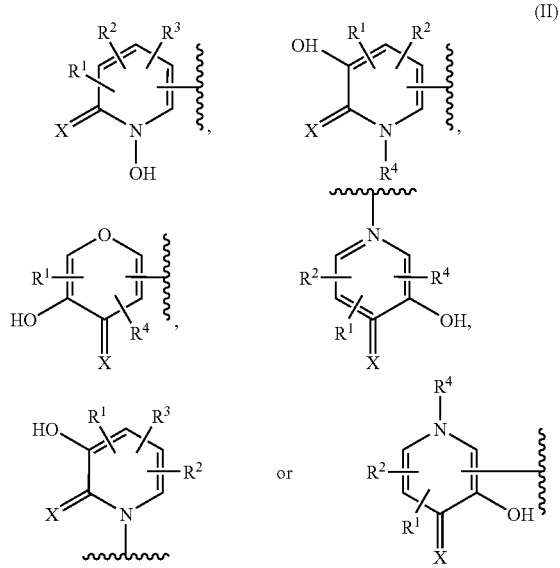

wherein X is O or S and each $R^1$, $R^2$, $R^3$, and $R^4$ is individually hydrogen or another substituent, or a pharmaceutically acceptable salt thereof. Preferably, at least one of $R^1$, $R^2$, $R^3$ and $R^4$ is an organic substituent.

In a further embodiment of the invention, at least one of $R^1$, $R^2$, $R^3$ or $R^4$ comprises one or more amido and/or amino moieties, including one or more peptidyl residues. For example, at least one of $R^1$, $R^2$, $R^3$ or $R^4$ can be a naturally-occurring peptide, a synthetic peptide, or a peptide analog (peptidomimetic), e.g., that comprises one or more amido moieties (—C(O)NH—).

Specific embodiments of the invention include compounds, wherein one or two of $R^1$, $R^2$, $R^3$ or $R^4$ is [[$(C_6$-$C_{10})$aryl]$_q$-[O]$_p$—[$(C_6$-$C_{10})$aryl]-[O]$_r$—[$(C_1$-$C_6)$alkyl]$_o$-[C(O)]$_s$—[N(R)]—[C(O)]$_t$—[$(C_1$-$C_6)$alkyl]$_w$-] (III) wherein q, p, r, o, s, t and w are individually is 0 or 1 and R is H, $(C_1$-$C_4)$alkyl, phenyl, or benzyl.

In specific embodiments of the invention;
preferably $(C_6$-$C_{10})$aryl is phenyl, preferably 1,4-phenylene;
preferably p, r, o, and w are 0 and s is 1;
preferably t is 1;
preferably t is 1 and w or o is 1, most preferably —CH$_2$—, —(CH$_2$)$_2$— or —(CH$_2$)$_3$—;
preferably p is 0, r is 0, o is —CH$_2$— or 0, s is 0, t is 1 and w is 0;
preferably q, p, r, and t or s are 0;
preferably q is 1, p is 1, o is 0, s is 0, t is 1 and w is 0;
preferably q is 0 or 1, p is 0 or 1, r is 0, o is 1, s is 0, t is 0 and w is 1; and
preferably q is 0 or 1, p is 0 or 1, r is 0 or 1, s is 0 or 1, t is 0 or 1 and w is 1, with the proviso that s and t are not both 1, when o is 0, w can be 0 or 1.

Preferably R is H or —CH$_3$—.

Preferably one of $R^1$, $R^2$, $R^3$ or $R^4$ is substituent (III); for example, one or two of $R^1$, $R^2$, $R^3$ or $R^4$ are individually biphenylcarbamyl, biphenylcarbamyl($C_1$-$C_6$)alkyl, biphenyl ($C_1$-$C_6$)alkylcarbamyl, biphenyl($C_1$-$C_6$)alkylcarbamyl ($C_1$-$C_6$)alkyl, phenoxyphenylcarbamyl, ($C_6$-$C_{10}$)aryl($C_1$-$C_6$) alkylamino($C_1$-$C_6$)alkyl, biphenyl($C_1$-$C_6$)alkylamino($C_1$-$C_6$)alkyl, ($C_6$-$C_{10}$)arylcarbonylamino($C_1$-$C_6$)alkyl, ($C_6$-$C_{10}$) aryl($C_1$-$C_6$)alkylcarbonylamino($C_1$-$C_6$)alkyl, biphenyloxy ($C_1$-$C_6$)alkylcarbonylamino($C_1$-$C_6$)alkyl, or phenoxyphenylcarbamyl($C_1$-$C_6$)alkyl, wherein the phenyl or aryl group(s) may be optionally substituted, or a pharmaceutically acceptable salt thereof.

The invention also provides a pharmaceutical composition, such as a unit dosage form, comprising a metalloprotein inhibitor (MPI) compound of the invention, or a pharmaceutically acceptable salt thereof, in combination with a pharmaceutically acceptable diluent or carrier, that can optionally include stabilizers, preservatives, buffers, and absorption control agents.

Additionally, the invention provides a therapeutic method for preventing or treating a pathology, condition or symptom in a mammal, such as a human, that is associated with pathological metalloprotein activity, such as a matrix metalloproteinase (MMP), histone deacetylase (HDAC) or anthrax lethal factor (LF) activity that is alleviated by inhibition of said activity, comprising administering to a mammal in need of such therapy, an effective amount of a metalloprotein inhibitor (MPI) of the invention, including a pharmaceutically acceptable salt thereof.

Also within the scope of the invention is a method of preparing a metalloprotein inhibitor (MPI), by covalently attaching a ZBG of formula (II) to one or more backbone molecules.

Additionally, many of the MPIs of the invention can be used as intermediates to prepare other MPIs of the invention.

SUMMARY OF THE FIGURES

FIG. 4. Summary table of IC$_{50}$ values (uM) for novel ZBGs against MMP-1, -2, and -3 measured using either a fluorescence- or colorimetric-based assay.

DETAILED DESCRIPTION OF THE INVENTION

Figure 1:
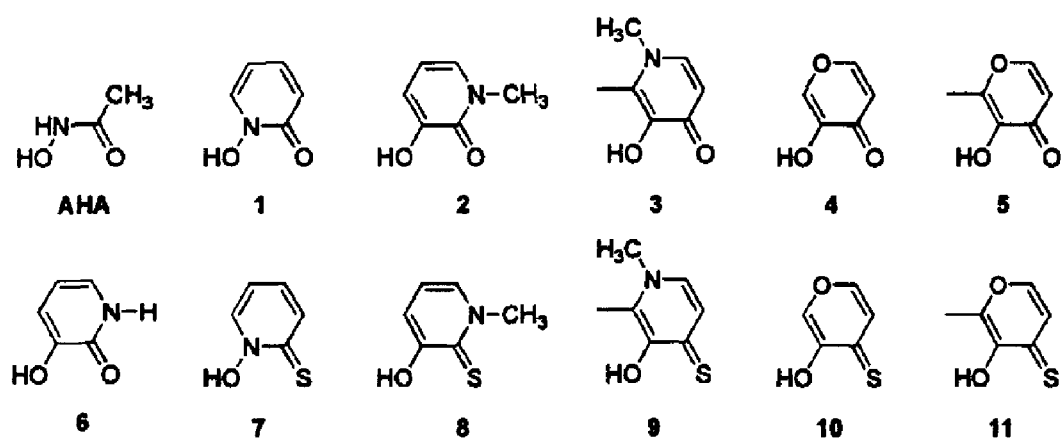
FIG. 1. Representative zinc-binding groups (ZBGs) (1-11). Acetohydroxamic acid (AHA) shown as reference.

Connective tissue, extracellular matrix constituents and basement membranes are required components of all mammals. These components are the biological materials that provide rigidity, differentiation, attachments and, in some cases, elasticity to biological systems including human beings and other mammals. Connective tissues components include, for example, collagen, elastin, proteoglycans, fibronectin and laminin. These biochemicals makeup, or are components of structures, such as skin, bone, teeth, tendon, cartilage, basement membrane, blood vessels, cornea and vitreous humor.

Under normal conditions, connective tissue turnover and/or repair processes are controlled and in equilibrium. The loss of this balance for whatever reason leads to a number of disease states. Inhibition of the enzymes responsible for loss of equilibrium provides a control mechanism for this tissue decomposition and, therefore, a treatment for these diseases.

Degradation of connective tissue or connective tissue components is carried out by the action of proteinase enzymes released from resident tissue cells and/or invading inflammatory or tumor cells. A major class of enzymes involved in this function is the MMPs.

The MMPs are divided into classes with some members having several different names in common use. Examples are: collagenase I (MMP-1, fibroblast collagenase; EC 3.4.24.3); collagenase II (MMP-8, neutrophil collagenase; EC 3.4.24.34), collagenase III (MMP-13), stromelysin 1 (MMP-3; EC 3.4.24.17), stromelysin 2 (MMP-10; EC 3.4.24.22), proteoglycanase, matrilysin (MMP-7), gelatinase A (MMP-2, 72 kDa gelatinase, basement membrane collagenase; EC 3.4.24.24), gelatinase B (MMP-9, 92 kDa gelatinase; EC 3.4.24.35), stromelysin 3 (MMP-11), metalloelastase (MMP-12, HME, human macrophage elastase) and membrane MMP (MMP-14). MMP is an abbreviation or acronym representing the term matrix metalloproteinase with the attached numerals providing differentiation between specific members of the MMP group.

Transcriptional regulation is key to normal functioning in biological systems including human beings and other mammals. Histones form the protein core of nucleosomes, which are DNA/protein complexes that are the subunits of eukaryotic chromatin. The histones are subject to a variety of post-translational modifications such as phosphorylation, ubiquitination and acetylation. These modifications have profound regulatory functions in gene transcription.

The packing and unpacking of nucelosomes as chromatins regulates gene expression. Acetylation of histones leads to an open chromatin structure and gene activation while the deacetylation of histones leads to a condensed chromatin structure and gene repression. The loss of this balance for whatever reason leads to a number of disease states. Inhibition of the enzymes responsible for the loss of equilibrium provides a control mechanism for transcription and gene expression or repression and, therefore, a treatment for these diseases. A major class of enzymes involved in regulation of transcription is (HDACs). HDAC is an abbreviation or acronym representing the term histone deacetylase with the attached numerals providing differentiation between specific members of the HDAC group.

The HDACs are divided into different classes with some members being $NAD^+$-dependent, sometimes referred to as sirutins. Examples are: HDAC1, HDAC4, HDAC6, HDAC11.

Anthrax lethal toxin, which is a combination of anthrax lethal factor and anthrax protective antigen, impairs multiple systems in the host including human beings and other mammals. Inactivation of the mitogen activated protein kinase (MAPK) signaling pathway in macrophages and dendritic cells impairs innate and adaptive immunity. This disruption of the MAPK pathway has many consequences for the host including but not limited to suppression of cytokine secretion, downregulation of costimulatory molecules, defective T and B cell priming, impaired p38 phosphorylation, endothelial cell apoptosis, macrophage apoptosis and suppression of inflammation.[15] Inhibition of enzymes responsible for these devastating effects provides a control mechanism and, therefore, a treatment for this disease. Anthrax lethal factor is involved in the effects of anthrax infection and the effects of anthrax lethal toxin.

Preferably the organic substituent(s) do(es) not substantially interfere with the ability of the moiety 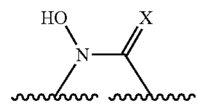 or 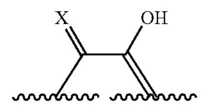 to bind to the metal ion of the target metalloprotein, such as the Zn(II) of a matrix metalloproteinase (MMP). Preferably, the organic radical(s) enhance(s) the ability of said moieties to bind to said Zn(II), or other metal ions.

Generally, the others of $R^1$, $R^2$, $R^3$ and $R^4$ are less bulky than the primary organic substituent(s), although 1-2 of $R^1$, $R^2$, or $R^3$ can be a second or third organic substituent in some instances. Thus, $R^1$, $R^2$, $R^3$, and $R^4$ are individually H, halo, CN, nitro, carboxyl, amino, sulfonamido, $(C_1\text{-}C_6)$alkyl, $(C_1\text{-}C_6)$alkoxy, $(C_3\text{-}C_6)$cycloalkyl, $(C_3\text{-}C_6)$cycloalkyl$(C_1\text{-}C_6)$alkyl), $(C_6\text{-}C_{10})$aryl, $(C_6\text{-}C_{10})$aryl$(C_2\text{-}C_{10})$alkyl, $(C_3\text{-}C_6)$heterocycloalkyl, $(C_3\text{-}C_6)$heterocycloalkyl$(C_1\text{-}C_6)$alkyl, $(C_2\text{-}C_6)$alkenyl, $(C_2\text{-}C_6)$alkynyl, $(C_1\text{-}C_6)$alkanoyl, halo$(C_1\text{-}C_6)$alkyl, hydroxy$(C_1\text{-}C_6)$alkyl, $(C_1\text{-}C_6)$alkoxycarbonyl, $(C_1\text{-}C_6)$alkylthio, thio$(C_1\text{-}C_6)$alkyl, $(C_1\text{-}C_6)$alkanoyloxy, biphenylcarbamyl, biphenylcarbamyl-$(C_1\text{-}C_6)$alkyl, biphenyl$(C_1\text{-}C_6)$alkylcarbamyl, biphenyl$(C_1\text{-}C_6)$alkylcarbamyl $(C_1\text{-}C_6)$alkyl, phenoxyphenylcarbamyl, $(C_6\text{-}C_{10})$aryl$(C_1\text{-}C_6)$alkylamino$(C_1\text{-}C_6)$alkyl, biphenyl$(C_1\text{-}C_6)$alkylamino$(C_1\text{-}C_6)$alkyl, $(C_6\text{-}C_{10})$arylcarbonylamino$(C_1\text{-}C_6)$alkyl, $(C_6\text{-}C_{10})$aryl$(C_1\text{-}C_6)$alkylcarbonylamino$(C_1\text{-}C_6)$alkyl, biphenyloxy $(C_1\text{-}C_6)$alkylcarbonylamino$(C_1\text{-}C_6)$alkyl, phenoxyphenylcarbamyl $(C_1\text{-}C_6)$alkyl, $N(R^6)(R^7)$ or $SO_2N(R^6)(R^7)$, wherein $R^6$ and $R^7$ are individually H, ═O, —OH, $(C_1\text{-}C_6)$alkyl, $(C_3\text{-}C_6)$cycloalkyl, $(C_3\text{-}C_6)$cycloalkyl$(C_1\text{-}C_6)$alkyl, phenyl or benzyl, or $R^6$ and $R^7$, together with the N to which they are attached, form a 5- or 6-membered ring which may optionally contain 1-2 S, $N(R^6)$ or nonperoxide O; or $R^1$ and $R^2$ together are methylenedioxy; optionally any of $R^1$, $R^2$, $R^3$, and $R^4$ is substituted with one to four $R^1$.

In one embodiment, one of $R^3$ or $R^4$ is $[[(C_6\text{-}C_{10})aryl]_q\text{-}[O]_q—[(C_6\text{-}C_{10})aryl]\text{-}[O]_q—[(C_1\text{-}C_6)alkyl]_q\text{-}[C(O)]_q—[N(R)]—[C(O)]_q—[(C_1\text{-}C_6)alkyl]_q\text{-}]$ wherein q is 0-1 and R is H, $(C_1\text{-}C_4)$alkyl, phenyl, or benzyl.

In another embodiment, one of $R^3$ or $R^4$ is $[[(C_6\text{-}C_{10})aryl]_q\text{-}[O]_q—[(C_6\text{-}C_{10})aryl]\text{-}[O]_q—[(C_1\text{-}C_6)alkyl]_q\text{-}[C(O)]_q—[N(R)]—[C(O)]_q—[(C_1\text{-}C_6)alkyl]_q\text{-}]$ wherein q is 0-1 and R is H, $(C_1\text{-}C_4)$alkyl, phenyl, or benzyl, and the ZBG is

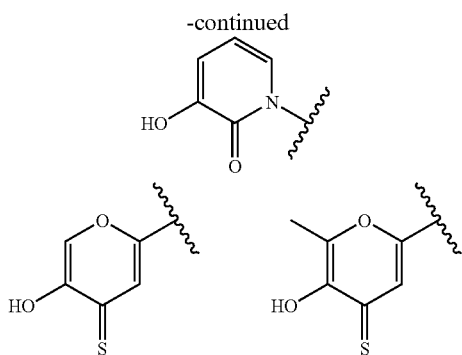

In a further embodiment, $R^3$ and $R^4$ are side chains that are individually biphenylcarbamyl, biphenylcarbamyl-$(C_1$-$C_6)$ alkyl, biphenyl$(C_1$-$C_6)$alkylcarbamyl, biphenyl$(C_1$-$C_6)$alkylcarbamyl $(C_1$-$C_6)$alkyl, phenoxyphenylcarbamyl, $(C_6$-$C_{10})$aryl$(C_1$-$C_6)$alkylamino$(C_1$-$C_6)$alkyl, biphenyl$(C_1$-$C_6)$alkylamino$(C_1$-$C_6)$alkyl, $(C_6$-$C_{10})$arylcarbonylamino$(C_1$-$C_6)$alkyl, $(C_6$-$C_{10})$aryl$(C_1$-$C_6)$alkylcarbonylamino$(C_1$-$C_6)$alkyl, biphenyl oxy$(C_1$-$C_6)$alkylcarbonylamino$(C_1$-$C_6)$alkyl, phenoxyphenylcarbamyl$(C_1$-$C_6)$alkyl, wherein the phenyl or aryl group(s) in the side chains may be optionally substituted with one to four $R^1$.

Exemplary side chains include biphenylmethylcarbamyl, phenoxyphenylcarbarnyl, biphenylcarbamyl, benzylaminomethyl, phenethylaminomethyl, benzoylaminomethyl, benzylcarbonylaminomethyl, phenethylcarbonylaminomethyl, phenylpropylcarbonylaminomethyl, biphenylmethylcarbamylmethyl, phenoxyphenylearbamylmethyl, biphenylcarbamylmethyl, and biphenylyloxyethylcarbonylaminomethyl, wherein the phenyl groups are optionally substituted with one to four $R^1$, Further embodiments of the invention include MPI compounds comprising ZBGs of formula (II) wherein the dangling valence is substituted by $R^7$, wherein $R^7$ is selected from $R^1$, $R^2$, or $R^3$. $R^7$ can also be a polymer chain, such as a polyanhydride, polylactone, polyether, polyester, polyamide, polyalkenylene, polyol, and the like.

As used herein, the term "treatment" of a metalloprotein-associated pathology, includes inhibiting metalloprotein activity such as HDAC, LF, or MMP activity in a subject exhibiting at least one of the symptoms of the onset of a metalloprotein-associated pathology or who is likely to develop such a pathology as well as the ability to halt or slow the progression of a metalloprotein-associated pathology or to reduce or alleviate at least one of the symptoms of said pathology.

A "therapeutic effect", "effective amount," or "therapeutic effective amount" is intended to qualify the amount of an anticancer agent according to the present invention required to relieve to some extent one or more of the symptoms and/or conditions of cancer, including, but is not limited to: 1) reduction in the number of cancer cells; 2) reduction in tumor size; 3) inhibition (i.e., slowing to some extent, preferably stopping) of cancer cell infiltration into peripheral organs; 4) inhibition (i.e., slowing to some extent, preferably stopping) of tumor metastasis; 5) inhibition, to some extent, of tumor growth; 6) relieving or reducing to some extent one or more of the symptoms associated with cancer; and/or 7) relieving or reducing the side effects associated with the administration of anticancer agents. The terms also are intended to qualify the amounts of anti-inflammatory agents or anti-anthrax lethal factor agents according to the present invention required to relieve to some extent one or more of the symptoms and/or conditions of diseases including, but not limited to arthritis (e.g., RA), restenosis, aortic aneurism, IBD, glomerular nephritis, MS, stroke, diabetes, bacterial meningitis, and graft vs. host disease. The terms also are intended to qualify the amounts of agents according to the present invention required to relieve to some extent one or more of the symptoms and/or conditions of diseases include epidermal scars, myocardial infarction, and periodontal disease.

The use of the term "about" in the present disclosure means "approximately," and encompasses variations in parameters that would arise during practice of the relevant art. Illustratively, the use of the term "about" indicates that dosages outside the cited ranges may also be effective and safe, and such dosages are also encompassed by the scope of the present claims.

The term "pharmaceutically acceptable" is used adjectivally herein to mean that the modified noun is appropriate for use in a pharmaceutical product.

The phrase "metalloprotein inhibitor" or "MPI" includes agents that specifically inhibit a class of enzymes such as MMP, HDAC, and LF. The MMPs are involved in the degradation of connective tissue or connective tissue components. These enzymes are released from resident tissue cells and/or invading inflammatory or tumor cells. Blocking the action of MMPs interferes with the creation of paths for newly forming blood vessels to follow. Examples of MMPi are described in Whittaker et at and is hereby incorporated by reference.[1]

The following definitions are used, unless otherwise described: halo is fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing about 5 or 6 ring atoms consisting of carbon and one to four heteroatoms each selected from the group consisting of non-peroxide oxygen, sulfur, and $N(R^7)$ wherein $R^7$ is absent or is as defined above; as well as a radical of an ortho-fused bicyclic heterocycle of about eight to ten ring atoms derived therefrom, particularly a benz-derivative or one derived by fusing a propylene, trimethylene, or tetramethylene diradical thereto.

Specific and preferred values listed below for radicals, substituents, and ranges, are for illustration only; they do not exclude other defined values or other values within defined ranges for the radicals and substituents.

Specifically, $(C_1$-$C_6)$alkyl can be methyl, ethyl, propyl, isopropyl, butyl, iso-butyl, sec-butyl, pentyl, 3-pentyl, or hexyl; $(C_3$-$C_{12})$cycloalkyl can be monocyclic, bicyclic or tricyclic and includes cyclopropyl, cyclobutyl, cyclopentyl, cyclohexyl, bicyclo[2.2.2]octanyl, norbornyl, adamantyl as well as various terpene and terpenoid structures. $(C_3$-$C_{12})$cycloalkyl$(C_1$-$C_6)$alkyl includes the foregoing cycloalkyl and can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl. Heterocycloalkyl and (heterocycloalkyl)alkyl include the foregoing cycloalkyl wherein the cycloalkyl ring system is monocyclic, bicyclic or tricyclic and optionally comprises 1-2 S, non-peroxide O or $N(R^7)$ as well as 2-12 ring carbon atoms; such as morpholinyl, piperidinyl, piperazinyl, indanyl, 1,3-dithian-2-yl, and the like; the cycloalkyl ring system optionally includes 1-3 double bonds or epoxy moieties and optionally is substituted with 1-3 OH, $(C_1$-$C_6)$alkanoyloxy, (CO), ($C_1$-$C_6$)alkyl or ($C_2$-$C_6$)alkynyl. ($C_1$-$C_6$)alkoxy can be methoxy, ethoxy, propoxy, isopropoxy, butoxy, iso-butoxy, sec-butoxy, pentoxy, 3-pentoxy, or hexyloxy; ($C_2$-$C_6$)alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; ($C_2$-$C_6$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; ($C_1$-$C_6$)alkanoyl can be formyl, acetyl, propanoyl or butanoyl; halo($C_1$-$C_6$)alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy($C_1$-$C_6$)alkyl can be alkyl substituted with 1 or 2 OH groups, such as hydroxymethyl, 1-hydroxyethyl, 2-hydroxyethyl, -hydroxypropyl, 2-hydroxypropyl, 3-hydroxypropyl, 1-hydroxybutyl, 4-hydroxybutyl, 3,4-dihydroxybutyl, 1-hydroxypentyl, 5-hydroxypentyl, 1-hydroxyhexyl, or 6-hydroxyhexyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_1$-$C_6$)alkylthio can be methylthio, ethylthio, propylthio, isopropylthio, butylthio, isobutylthio, pentylthio, or hexylthio; ($C_2$-$C_6$)alkanoyloxy can be acetoxy, propanoyloxy, butanoyloxy, isobutanoyloxy, pentanoyloxy, or hexanoyloxy; aryl can be phenyl, indenyl, indanyl, or naphthyl; and heteroaryl can be furyl, imidazolyl, triazolyl, triazinyl, oxazolyl, isoxazolyl, thiazolyl, isothiazolyl, pyrazolyl, pyrrolyl, pyrazinyl, tetrazolyl, pyridyl, (or its N-oxide), thienyl, pyrimidinyl (or its N-oxide), 1H-indolyl, isoquinolyl (or its N-oxide) or quinolyl (or its N-oxide).

Optionally, any of $R^1$, $R^2$, or $R^3$ can be substituted by one to three $R^1$ (except for H, halo or CN).

Preferably, one of $R^1$, $R^2$, or $R^3$ is ($C_1$-$C_3$)alkyl.

Preferably, one of $R^1$, $R^2$, or $R^3$ is H.

Preferably, $R^4$ is ($C_1$-$C_3$)alkyl, benzyl, t-Boc, ($C_3$-$C_6$)cycloalkyl($C_1$-$C_3$)alkyl, or H.

Figure 5:
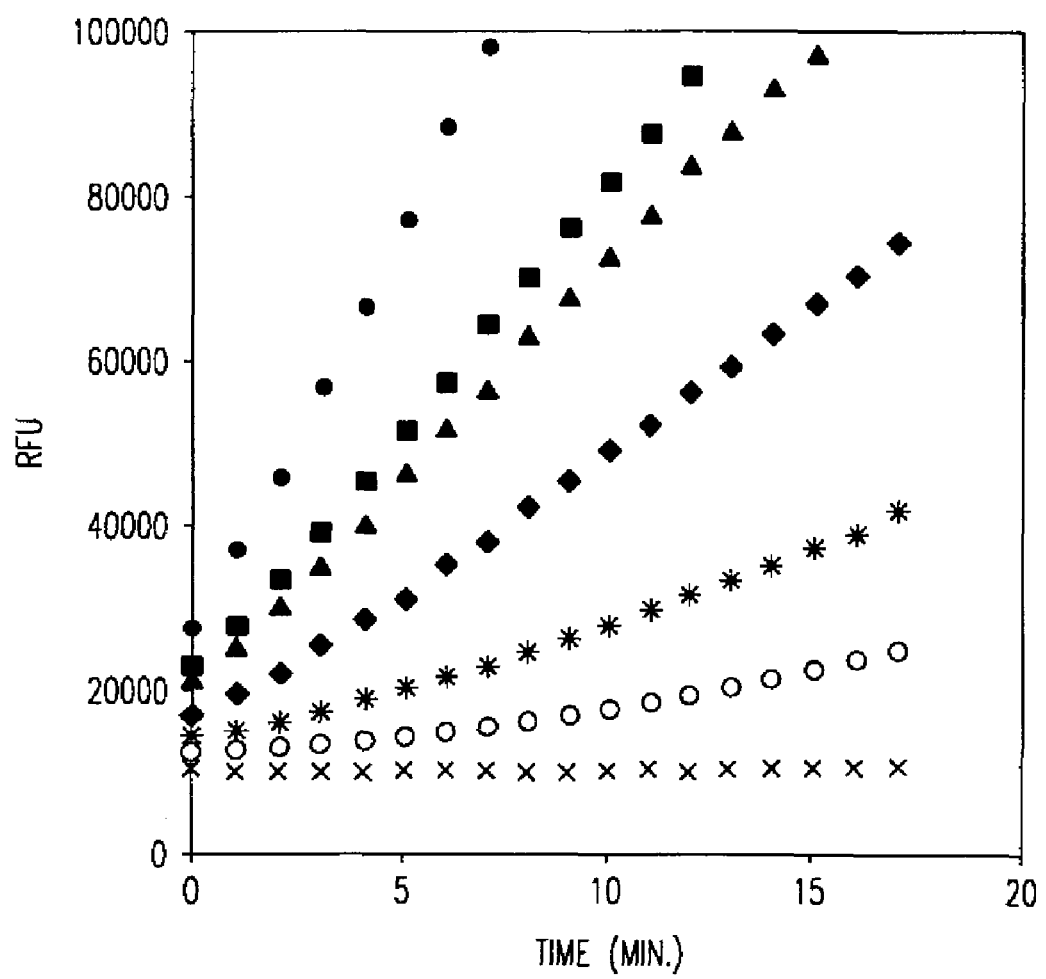
FIG. 5. Raw data from fluorescent assay of 11 with MMP-3. Relative fluorescent units (RFU) produced from substrate cleavage in each reaction well: control (0 mM 11, circles ●), 11 0.05 mM (squares ■), 11 0.1 mM (triangles ▲), 11 0.2 mM (diamonds ♦), 11 0.3 mM (*), 11 0.5 mM (○), and 11 1.0 mM (x) are plotted versus time in minutes FIG. 6. IC$_{50}$ plot of 11. The slopes of kinetic traces from the plot shown in FIG. 5 containing inhibitor are compared to the slope of the control (no inhibitor). The [(inhibitor slope/control slope)×100] (% Control) is plotted versus inhibitor concentration. A linear fit of the data for each experiment (three experiments shown in FIG. 6) gives the IC$_{50}$ value of the inhibitor where y=50%.
Figure 6:
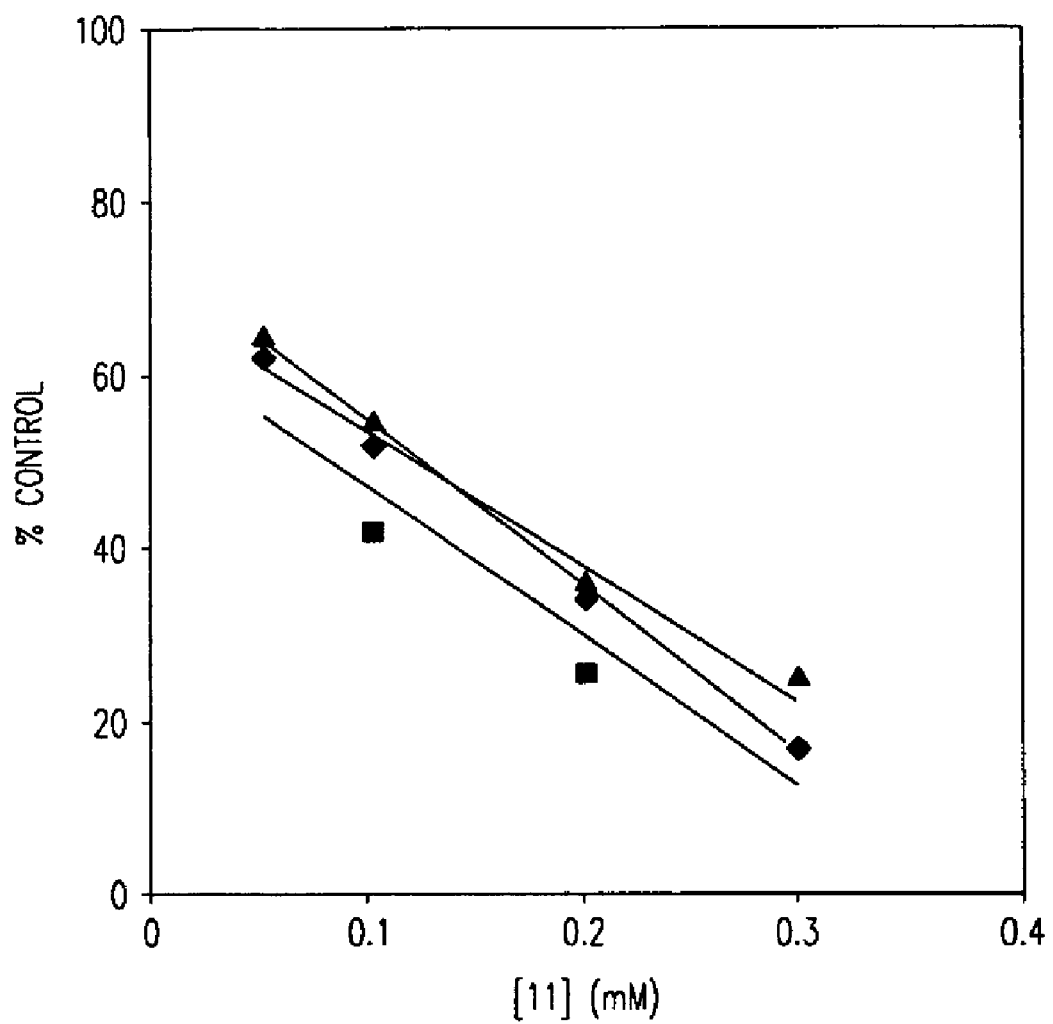

Useful backbone molecules comprise organic substituents having the structural features depicted in FIG. 5 and FIG. 6 of Whittaker et al.,[1] wherein the moiety HON(H)—C(O)—CH($R_a$)— has been replaced with a ZBG of formula (I), or the structural features depicted in the claims of EPA 126,974, wherein at least the moiety $COR^1$ has been replaced by a ZBG of formula (I).

The structure of the organic backbone molecule(s) and other organic substituents preferably do not interfere with and, preferably enhance the ability of the MPI to direct the ZBG toward one or more complexed metal ions, such as Zn(II) atoms of the MMP. For example, Pep can be any of the organic radicals derived from the structures shown on Scheme 1 of the Whittaker et. al.,[1] after removal of the C(O)NH(OH) group, or in the claims of published European patent application No. 126,974, after removal of $COR^1$.

The organic backbone molecule and/or organic substituent(s) can be a naturally-occurring peptide, a synthetic peptide or a peptide analog (peptidomimetic). Such groups may comprise one or more amido moieties (—C(O)NH—), which can be or comprise, peptidyl bonds, e.g., amide bonds formed by reaction of the amino group of an alpha-aminocarboxylic acid with the carboxy group of a second amino acid.

For example, embodiments of the compound of formula (I) or (II) can be represented by [ZBG]-C($R^5$)($R^6$)—C(O)NH—, [ZBG]-C($R^8$)—C(O)N(H)—CH($R^9$)—C(O)NH($R^{10}$), or [ZBG-C($R^5$)($R^6$)—C(O)N(H)—CH($R^9$)—C(O)NH($R^{10}$), wherein ZBG comprises the heterocyclic ring of formula (I) or (II) $R^8$, $R^9$ and $R^{10}$ correspond to $R^1$, $R^2$ and $R^3$ respectively, and wherein $R^5$ is H and $R^6$ is ($C_1$-$C_{22}$)alkyl, ($C_2$-$C_6$)alkenyl, ($C_6$-$C_{10}$)aryl, ($C_1$-$C_6$)alkyl, ($C_6$-$C_{10}$)heteroaryl, ($C_6$-$C_{10}$)heteroaryl($C_1$-$C_6$)alkyl, ($C_3$-$C_6$)cycloalkyl, ($C_3$-$C_6$)cycloalkyl($C_1$-$C_6$)alkyl, or $R^5$ and $R^6$ together with the carbon atom to which they are attached can be ($C_4$-$C_6$) spiroalkyl or spiroheterocycloalkyl. In certain embodiments of the invention, peptidyl or peptidomimetic substituents are terminated by a ZBG of formula (I) or (II), and optionally, the other terminus is C(O)N($R^6$)($R^7$).

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine anti-toxin activity using the standard tests described herein, or using other similar tests which are well known in the art.

In cases where compounds are sufficiently basic or acidic to form stable nontoxic acid or base salts, administration of the compounds as salts may be appropriate. Pharmaceutically acceptable salts may be obtained using standard procedures well known in the art, for example by reacting a sufficiently basic compound such as an amine with a suitable acid affording a physiologically acceptable anion.

Pharmaceutically acceptable salts include metallic ions and organic ions. More preferred metallic ions include, but are not limited to appropriate alkali metal (Group Ia) salts, for example, sodium potassium, or lithium, and alkaline earth metal (Group IIa) salts, for example, calcium, and other physiological acceptable metal ions. Exemplary ions include aluminum, calcium, lithium, magnesium, potassium, sodium and zinc in their usual valences. Preferred organic ions include protonated tertiary amines and quaternary ammonium cations, including in part, trimethylamine, diethylamine, N,N-dibenzylethylenediamine, chloroprocaine, choline, diethanolamine, ethylenediamine, meglumine (N-methylglucamine) and procaine.

Illustrative pharmaceutically acceptable salts are prepared from hydrochloric, hydrobromic, phosphoric, sulfuric, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxy-ethanesulfonic, sulfanilic, cyclohexylaminosulfonic, algesic, β-hydroxybutyric, galactaric and galacturonic acids.

The compositions of the present invention are usually administered in the form of pharmaceutical compositions. These compositions can be administered by any appropriate route including, but not limited to, oral, nasogastric, rectal, transdermal, parenteral (for example, subcutaneous, intramuscular, intravenous, intramedullary, intrasternal, and intradermal injections, or infusion techniques), intranasal, transmucosal, implantation, vaginal, topical, buccal, and sublingual administration. Such preparations may routinely contain buffering agents, preservatives, penetration enhancers, compatible carriers, and other therapeutic or non-therapeutic ingredients.

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and non-ionic detergents, or polyethylene glycols can be used. Mixtures of solvents and wetting agents such as those discussed above are also useful.

Suppositories for rectal administration of the drug can be prepared by mixing the drug with a suitable nonirritating excipient such as cocoa butter, synthetic mono-, di- or triglycerides, fatty acids and polyethylene glycols that are solid at ordinary temperatures but liquid at the rectal temperature and will therefore melt in the rectum and release the drug.

Solid dosage forms for oral administration can include capsules, ingestible tablets, buccal tablets, troches, dragées, pills, powders, granules, and wafers. In such solid dosage forms, the compounds of this invention are ordinarily combined with one or more adjuvants appropriate to the indicated route of administration. The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, granules, or capsules may be coated with gelatin, wax, shellac or sugar and the like. The tablets, pills, granules, or capsules comprising the inventive compositions may be film coated or enteric-coated.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina, and the like. Useful liquid carriers include water, alcohols or glycols, or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of active ingredient that can be combined with the carrier materials to produce a single dosage form varies depending upon the mammalian host treated and the particular mode of administration.

The present invention also includes methods employing a pharmaceutical composition that contains the composition of the present invention associated with pharmaceutically acceptable carriers or excipients. As used herein, the terms "pharmaceutically acceptable carrier" or "pharmaceutically acceptable excipients" includes any and all solvents, dispersion media, coatings, antibacterial and antifungal agents, isotonic and absorption delaying agents, and the like. The use of such media and agents for ingestible substances is well known in the art. Except insofar as any conventional media or agent is incompatible with the compositions, its use is contemplated. Supplementary active ingredients can also be incorporated into the compositions. In making the compositions of the present invention, the compositions(s) can be mixed with a pharmaceutically acceptable excipient, diluted by the excipient or enclosed within such a carrier, which can be in the form of a capsule, sachet, or other container. The carrier materials that can be employed in making the composition of the present invention are any of those commonly used excipients in pharmaceutics and should be selected on the basis of compatibility with the active drug and the release profile properties of the desired dosage form.

Illustratively, pharmaceutical excipients are chosen below as examples:

(a) Binders such as acacia, alginic acid and salts thereof, cellulose derivatives, methylcellulose, hydroxyethyl cellulose, hydroxypropyl cellulose, magnesium aluminum silicate, polyethylene glycol, gums, polysaccharide acids, bentonites, hydroxypropyl methylcellulose, gelatin, polyvinylpyrrolidone, polyvinylpyrrolidone/vinyl acetate copolymer, crospovidone, povidone, polymethacrylates, hydroxypropylmethylcellulose, hydroxypropylcellulose, starch, pregelatinized starch, ethylcellulose, tragacanth, dextrin, microcrystalline cellulose, sucrose, or glucose, and the like.

(b) Disintegration agents such as starches, pregelatinized corn starch, pregelatinized starch, celluloses, cross-linked carboxymethylcellulose, sodium starch glycolate, crospovidone, cross-linked polyvinylpyrrolidone, croscarmellose sodium, microcrystalline cellulose, a calcium, a sodium alginate complex, clays, alginates, gums, or sodium starch glycolate, and any disintegration agents used in tablet preparations.

(c) Filling agents such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

(d) Surfactants such as sodium lauryl sulfate, sorbitan monooleate, polyoxyethylene sorbitan monooleate, polysorbates, polaxomers, bile salts, glyceryl monostearate, Pluronic™ line (BASF), and the like.

(e) Solubilizer such as citric acid, succinic acid, fumaric acid, malic acid, tartaric acid, maleic acid, glutaric acid sodium bicarbonate and sodium carbonate and the like.

(f) Stabilizers such as any antioxidation agents, buffers, or acids, and the like, can also be utilized.

(g) Lubricants such as magnesium stearate, calcium hydroxide, talc, sodium stearyl fumarate, hydrogenated vegetable oil, stearic acid, glyceryl behapate, magnesium, calcium and sodium stearates, stearic acid, talc, waxes, Stearowet, boric acid, sodium benzoate, sodium acetate, sodium chloride, DL-leucine, polyethylene glycols, sodium oleate, or sodium lauryl sulfate, and the like.

(h) Wetting agents such as oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, or sodium lauryl sulfate, and the like.

(i) Diluents such lactose, starch, mannitol, sorbitol, dextrose, microcrystalline cellulose, dibasic calcium phosphate, sucrose-based diluents, confectioner's sugar, monobasic calcium sulfate monohydrate, calcium sulfate dihydrate, calcium lactate trihydrate, dextrates, inositol, hydrolyzed cereal solids, amylose, powdered cellulose, calcium carbonate, glycine, or bentonite, and the like.

(j) Anti-adherents or glidants such as talc, corn starch, DL-leucine, sodium lauryl sulfate, and magnesium, calcium, or sodium stearates, and the like.

(k) Pharmaceutically compatible carrier comprises acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, or pregelatinized starch, and the like.

Additionally, drug formulations are discussed in, for example, Remington's The Science and Practice of Pharmacy (2000). Another discussion of drug formulations can be found in Liberman, H. A. and Lachman, L., Eds., Pharmaceutical Dosage Forms, Marcel Decker, New York, N.Y., 1980.

Besides being useful for human treatment, the present invention is also useful for other subjects including veterinary animals, reptiles, birds, exotic animals, and farm animals, including mammals, rodents, and the like. Mammal includes a primate, for example, a monkey, or a lemur, a horse, a dog, a pig, or a cat. A rodent includes a rat, a mouse, a squirrel, or a guinea pig.

Additionally, the invention provides a therapeutic method for preventing or treating a pathological disease, condition or symptom in a mammal, such as a human, that is associated with pathological metalloprotein activity, such as a matrix metalloproteinase (MMP), histone deacetylase (HDAC) or anthrax lethal factor (LF) activity that is alleviated by inhibition of said activity, comprising administering to a mammal in need of such therapy, an effective amount of a metalloprotein inhibitor (MPI) of the invention, including a pharmaceutically acceptable salt thereof.

Such conditions, disease or symptoms include cancer, anthrax pathogenesis associated with anthrax lethal factor, and the inflammatory pathologies set forth in Whitaker, et al. or EPA 126,974, cited above, including arthritis (e.g., RA), restenosis, aortic aneurism, IBD, glomerular nephritis, MS, stroke, diabetes, bacterial meningitis, and graft vs. host disease. Cancers amenable to treatment include leukemia, myeloma, lymphoma, metastatic breast or metastatic prostate cancer, Hodgkin's lymphoma, non-Hodgkin's lymphoma, osteosarcoma, germ cell tumor, lung cancer, ovarian cancer, pancreatic cancer, renal cell carcinoma, melanoma, myelodysplastic syndrome, Ewing's sarcoma, and Paget's disease. Other conditions or diseases amenable to treatment include epidermal scars, myocardial infarction, and periodontal disease.

For treatment of a pathological disease, condition, or symptom associated with pathological metalloprotein activity, such as a matrix metalloproteinase (MMP) activity, histone deacetylase activity (HDAC), or lethal factor activity (LF), and/or that is alleviated by inhibition of said activity, compositions of the invention can be used to provide a dose of a compound of the present invention in an amount sufficient to elicit a therapeutic response, e.g., inhibition of tumor growth, for example a dose of about 5 ng to about 1000 mg, or about 100 ng to about 600 mg, or about 1 mg to about 500 mg, or about 20 mg to about 400 mg. Typically a dosage effective amount will range from about 0.0001 mg/kg to 1500 mg/kg, more preferably 1 to 1000 mg/kg, more preferably from about 1 to 150 mg/kg of body weight, and most preferably about 50 to 100 mg/kg of body weight. A dose can be administered in one to about four doses per day, or in as many doses per day to elicit a therapeutic effect. Illustratively, a dosage unit of a composition of the present invention can typically contain, for example, about 5 ng, 50 ng 100 ng, 500 ng, 1 mg, 10 mg, 20 mg, 40 mg, 80 mg, 100 mg, 125 mg, 150 mg, 200 mg, 250 mg, 300 mg, 350 mg, 400 mg, 450 mg, 500 mg, 550 mg, 600 mg, 700 mg, 800 mg, 900 mg, or 1000 mg of a compound of the present invention. The dosage form can be selected to accommodate the desired frequency of administration used to achieve the specified dosage. The amount of the unit dosage form of the composition that is administered and the dosage regimen for treating the condition or disorder depends on a variety of factors, including, the age, weight, sex and medical condition, of the subject, the severity of the condition or disorder, the route and frequency of administration, and this can vary widely, as is well known.

In one embodiment of the present invention, the composition is administered to a subject in an effective amount, that is, the composition is administered in an amount that achieves a therapeutically effective dose of a compound of the present invention in the blood serum of a subject for a period of time to elicit a desired therapeutic effect. Illustratively, in a fasting adult human (fasting for generally at least 10 hours) the composition is administered to achieve a therapeutically effective dose of a compound of the present invention in the blood serum of a subject from about 5 minutes alter administration of the composition. In another embodiment of the present invention, a therapeutically effective dose of the compound of the present invention is achieved in the blood serum of a subject at about 10 minutes from the time of administration of the composition to the subject. In another embodiment of the present invention, a therapeutically effective dose of the compound of the present invention is achieved in the blood serum of a subject at about 20 minutes from the time of administration of the composition to the subject. In yet another embodiment of the present invention, a therapeutically effective dose of the compound of the present invention is achieved in the blood serum of a subject at about 30 minutes from the time of administration of the composition to the subject. In still another embodiment of the present invention, a therapeutically effective dose of the compound of the present invention is achieved in the blood serum of a subject at about 40 minutes from the time of administration of the composition to the subject. In one embodiment of the present invention, a therapeutically effective dose of the compound of the present invention is achieved in the blood serum of a subject at about 20 minutes to about 12 hours from the time of administration of the composition to the subject. In another embodiment of the present invention, a therapeutically effective dose of the compound of the present invention is achieved in the blood serum of a subject at about 20 minutes to about 6 hours from the time of administration of the composition to the subject. In yet another embodiment of the present invention, a therapeutically effective dose of the compound of the present invention is achieved in the blood serum of a subject at about 20 minutes to about 2 hours from the time of administration of the composition to the subject. In still another embodiment of the present invention, a therapeutically effective dose of the compound of the present invention is achieved in the blood serum of a subject at about 40 minutes to about 2 hours from the time of administration of the composition to the subject. And in yet another embodiment of the present invention, a therapeutically effective dose of the compound of the present invention is achieved in the blood serum of a subject at about 40 minutes to about 1 hour from the time of administration of the composition to the subject.

In one embodiment of the present invention, a composition of the present invention is administered at a dose suitable to provide a blood serum concentration with a half maximum dose of a compound of the present invention. Illustratively, a blood serum concentration of about 0.01 to about 1000 nM, or about 0.1 to about 750 nM, or about 1 to about 500 nM, or about 20 to about 1000 nM, or about 100 to about 500 nM, or about 200 to about 400 nM is achieved in a subject after administration of a composition of the present invention.

Contemplated compositions of the present invention provide a therapeutic effect as compound of the present invention medications over an interval of about 5 minutes to about 24 hours after administration, enabling once-a-day or twice-a-day administration if desired. In one embodiment of the present invention, the composition is administered at a dose suitable to provide an average blood serum concentration with a half maximum dose of a compound of the present invention of at least about 1 µg/ml, or at least about 5 µg/ml, or at least about 10 µg/ml, or at least about 50 µg/ml, or at least about 100 µg/ml, or at least about 500 µg/ml, or at least about 1000 µg/ml in a subject about 10, 20, 30, or 40 minutes after administration of the composition to the subject.

The amount of therapeutic agent necessary to elicit a therapeutic effect can be experimentally determined based on, for example, the absorption rate of the agent into the blood serum, the bioavailability of the agent, and the potency for treating the disorder. It is understood, however, that specific dose levels of the therapeutic agents of the present invention for any particular subject depends upon a variety of factors including the activity of the specific compound employed, the age, body weight, general health, sex, and diet of the subject (including, for example, whether the subject is in a fasting or fed state), the time of administration, the rate of excretion, the drug combination, and the severity of the particular disorder being treated and form of administration. Treatment dosages generally may be titrated to optimize safety and efficacy. Typically, dosage-effect relationships from in vitro and/or in vivo tests initially can provide useful guidance on the proper doses for subject administration. Studies in animal models generally may be used for guidance regarding effective dosages for treatment of diseases in accordance with the present invention. In terms of treatment protocols, it should be appreciated that the dosage to be administered will depend on several factors, including the particular agent that is administered, the route administered, the condition of the particular subject, etc. Generally speaking, one will desire to administer an amount of the compound that is effective to achieve a serum level commensurate with the concentrations found to be effective in vitro for a period of time effective to elicit a therapeutic effect. Thus, where a compound is found to demonstrate in vitro activity at, for example, a half-maximum effective dose of 200 nM, one will desire to administer an amount of the drug that is effective to provide about a half-maximum effective dose of 200 nM concentration in vivo for a period of time that elicits a desired therapeutic effect, for example, treating a disorder related to high beta-amyloid-induced neurotoxicity and other indicators as are selected as appropriate measures by those skilled in the art. Determination of these parameters is well within the skill of the art. These considerations are well known in the art and are described in standard textbooks.

In order to measure and determine the effective amount of a compound of the present invention to be delivered to a subject, serum concentrations of a compound of the present invention can be measured using standard assay techniques.

Contemplated compositions of the present invention provide a therapeutic effect over an interval of about 30 minutes to about 24 hours after administration to a subject. In one embodiment compositions provide such therapeutic effect in about 30 minutes. In another embodiment compositions provide therapeutic effect over about 24 hours, enabling once-a-day administration to improve patient compliance.

The present methods and compositions can also be used in combination ("combination therapy") with another pharmaceutical agent that is indicated for treating cancer, anthrax pathogenesis associated with anthrax lethal factor, and the inflammatory pathologies and other conditions or diseases set forth above.

Tris(pyrazolyl)borate Model Complexes. Previous work has shown that tris(pyrazolyl)borate complexes of zinc provide an accurate model for the tris(histidine) active site of several metalloproteins including MMPs.[16-20] In addition, studies on these model compounds have shown that acetohydroxamic acid forms a complex that is structurally identical to the coordination environment of hydroxamate-based drugs bound to the catalytic zinc(II) ion in MMPs.[16,21] Using this same model, the interaction of ZBGs from identified inhibitors was evaluated where the mode of binding was unknown.[16] This study proved to be very informative, because a direct correlation between the inhibitory activity and mode of binding was found.[10] These observations further validate the use of model complexes as an effective strategy for determining, at a molecular level, the interactions between inhibitors and MMPs.

Figure 2A:
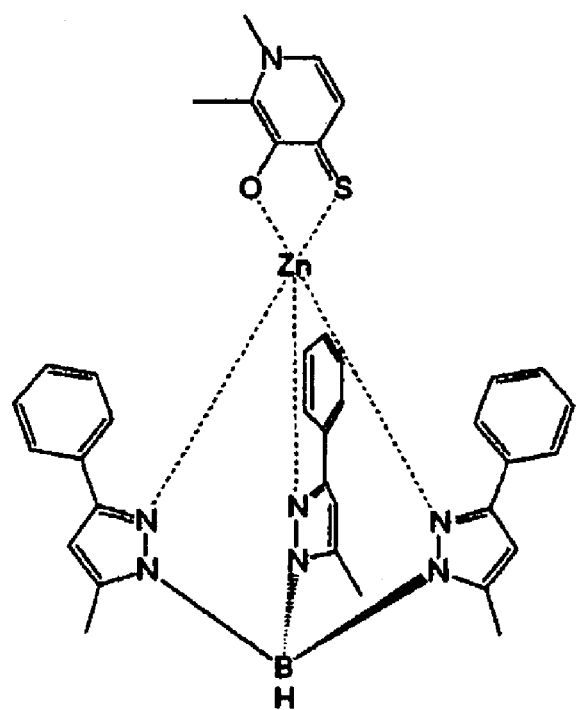
FIG. 2A. Chemical (top) and 2B structural (bottom, 50% probability ellipsoids) diagram of [(Tp$^{Ph,Me}$)Zn(9)] showing the chelation of the O,S ligand to the zinc(II) ion. Hydrogen atoms have been omitted for clarity.
Figure 2B:
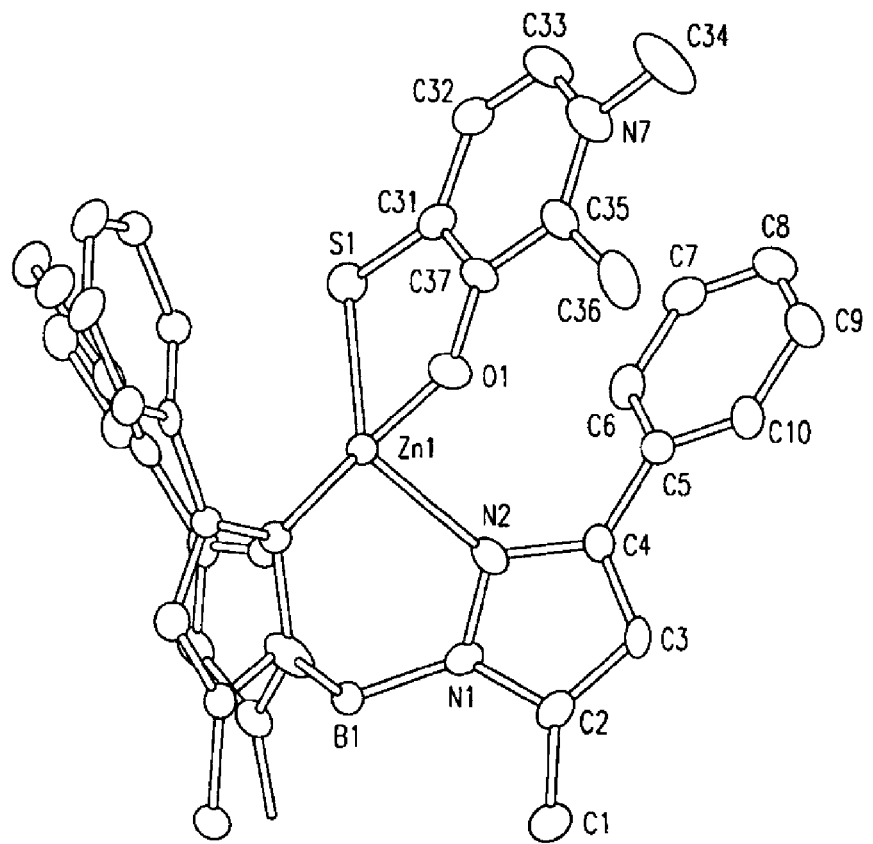

Tris(pyrazolyl)borate complexes of zinc(II) can be used as an initial screen for ZBGs by providing structural and qualitative binding information without the need for sophisticated drug synthesis or protein structure determination. The structures show (FIG. 2 shows a representative example) that all of the novel ZBGs in FIG. 1 can coordinate the zinc(II) ion in a bidentate fashion.[17,22] The metal-ligand bond lengths are compared to those found in the corresponding acetohydroxamate complex.[10] These model-based studies further support the invention described here and are believed to provide additional characterization for the mode of action of these metal chelators toward metalloproteins and MPI design.

Unless otherwise noted, starting materials were obtained from commercial suppliers (e.g., Aldrich), have been reported in the scientific literature, or can be prepared from readily available starting materials using procedures known in the field. Commercially available starting materials were used without further purification. The abbreviation DMAP stands for 4-dimethylaminopyridine; TBSCI stands for tert-butyldimethylsilyl chloride; HMDO stands for hexamethyldisiloxane. $^1$H/$^{13}$C NMR spectra were recorded on a Varian FT-NMR spectrometer running at 300 or 400 MHz at the Department of Chemistry and Biochemistry, University of California, San Diego. Infrared spectra were collected on a Nicolet AVATAR 320 FT-IR instrument at the Department of Chemistry and Biochemistry, University of California, San Diego. Illustrative syntheses are disclosed in Schemes 1-5 hereinbelow:

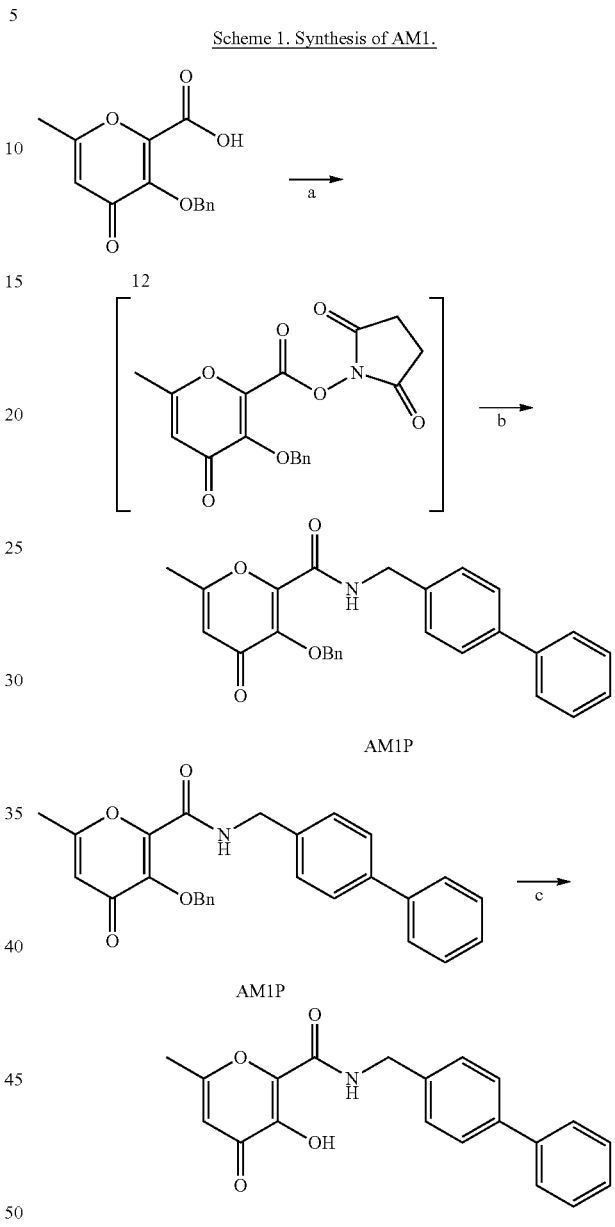

a) NHS, DCC, dry THF, RT; b) 4-phenylbenzylamine, dry THF, RT, 88%(2 steps); c) Pd/C 10%, H$_2$ 35 psi, MeOH, RT, 60%.

2-Carboxy-3-benzyloxy-6-methyl-pyran-4(1H)-one (12). was synthesized according to a previous procedure.[23]

NHS activation of 2-Carboxy-3-benzyloxy-6-methyl-pyran-4(1H)-one. To a solution of (12) (300 mg 1.15 mmol) in dry THF (15 mL) was added NHS (133 mg 1.15 mmol). The reaction mixture was stirred for 30 minutes at room temperature under a N$_2$(g) atmosphere. DCC (238 mg 1.15 mmol) was added to the stirring solution and the mixture was continued to stir for 3 hours until TLC showed consumption of starting material. The DCU was filtered and the resulting filtrate was used in situ to synthesize AM1-3.

AM1P. To the above solution was added phenyl benzyl amine (210 mg 1.15 mmol) in THF (15 mL) dropwise. The reaction was stirred at room temperature over night under a N₂(g) atmosphere. The product precipitated as a white solid, which was filtered, washed with 20 mL methanol and dried to yield 430 mg. Yield 88% ¹H NMR (400 MHz d-DMSO) δ 2.9 (s, 3H, CH₃), 4.4 (d, J=6.0 Hz, 2H, CH₂), 5.1 (s, 2H, benzyl-CH₂), 6.4 (s, 1H, pyrone-H), 7.3 (m, 8H, phenyl-H), 7.5 (t, J=14.8 Hz, 2H, phenyl-H), 7.6 (d, J=6.0 Hz 2H, phenyl-H), 7.7 (d, J=6.0 Hz 2H, phenyl-H), 9.5 (t, J=12 Hz, 1H, amide-H). (+)-ESIMS: m/z 448.07 [M+Na]⁺.

AM1. To a suspension of AM1P (100 mg 0.24 mmol) in ethanol (50 mL) was added 10 mg of 10% Pd/C and placed under H₂ at 35 psi overnight at room temperature. The catalyst was filtered off and the filtrate was evaporated to an off-white solid, which was washed with 20 mL benzene, recrystallized from ethanol and dried to yield 60 mg of a white solid. Yield 76% ¹H NMR. (400 MHz d-MeOH) δ 2.4 (s, 3H, CH₃), 4.6 (br, 2H, CH₂), 6.3 (s, 1H, pyrone-H), 7.3 (t, J=12 Hz 1H, phenyl-H), 7.4 (m, 4H, phenyl-H), 7.6 (m, 4H, phenyl-H). Anal. Calcd. (found) for C₂₀H₁₇NO₄.0.25 CH₃CH₂OH: C, 70.98 (70.68) H, 5.38 (5.76) N, 4.04 (4.44).

AM2P. The same general procedure was used as in the synthesis of AM1P with the exception that the reaction was stirred for 6 days at room temperature. ¹H NMR (400 MHz d-DMSO) δ 2.4 (s, 3H, CH₃), 5.5 (s, 2H, benzyl- CH₂), 6.3 (s, 1H, pyrone-H), 6.9 (d, J=8.7 Hz, 2H, phenyl-H), 7.0 (d, J=7.8 Hz, 2H, phenyl-H), 7.1 (m, 3H, phenyl-H), 7.4 (m, 7H, phenyl-H), 9.7 (br, 1H, amide-H). FABHRMS: theoretical [M+H]⁺: 428.1492, calc. [M+H]⁺: 428.1498.

AM3P. The same general procedure was used as in the synthesis of AM2P. Yield 40% ¹H NMR (400 MHz CDCl₃) δ 2.4 (s, 3H, CH₃), 5.5 (s, 2H, benzyl- CH₂), 6.3 (s, 1H, pyrone-H), 7.2 (d, J=8.7 Hz, 2H, phenyl-H), 7.3 (m, 2H, phenyl-H), 7.4 (m, 4H, phenyl-H), 7.5 (m, 4H, phenyl-H), 7.2 (d, J=6.8 Hz, 2H, phenyl-H), 9.8 (br, 1H, amide-H). (+)-ESIMS: m/z 434.04 [M+Na]⁺.

AM3. The same general procedure was used as in the synthesis of AM1 Yield 77% ¹H NMR (300 MHz d-MeOH) δ 2.5 (s, 3H, CH₃), 6.4 (s, 1H, pyrone-H), 7.3 (d, J=6.9 Hz, 1H, phenyl-H), 7.4 (t, J=15.0 Hz, 2H, phenyl-H), 7.6 (t, J=16.2 Hz, 1H, phenyl-H), 7.8 (d, J=8.7 Hz, 1H, phenyl-H). (+)-ESIMS: m/z 422.06 [M+H]⁺.

Anal. Calcd. (found) for C₂₀H₁₇NO₄.0.5 CH₃CH₂OH: C, 69.76 (69.54) H, 5.27 (5.48) N, 4.07 (4.30).

Scheme 2. Synthesis of CA1.

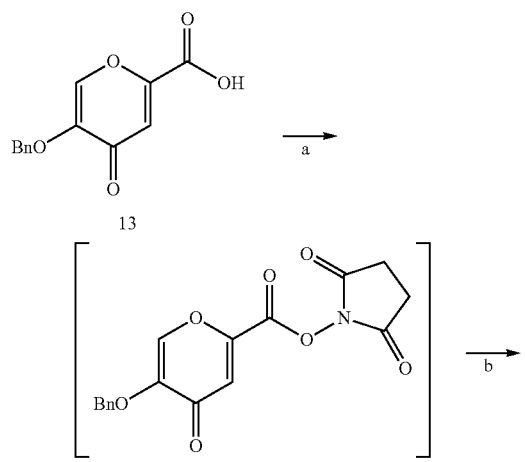

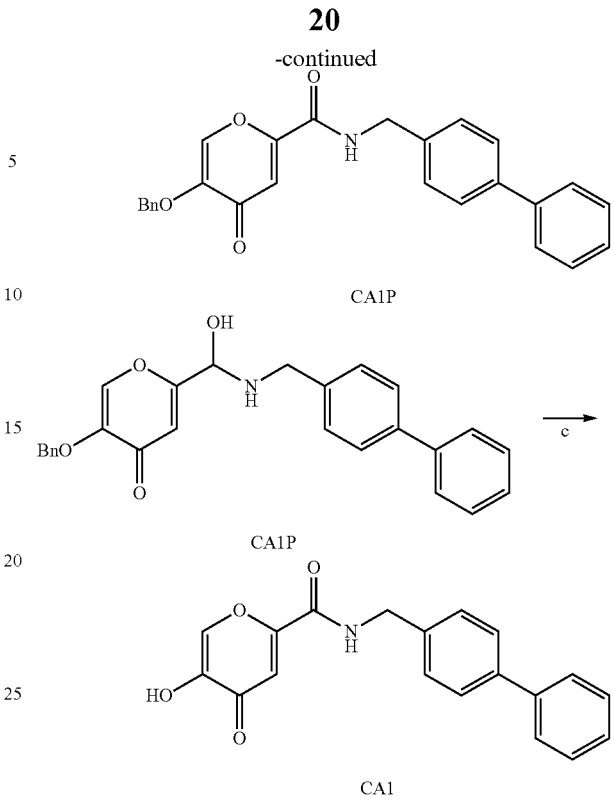

a) NHS, DCC, dry THF, RT; b) 4-phenylbenzylamine, dry THF, 80%(2 steps);
c) Pd/C 10%, H₂ 35 psi, MeOH, RT, 75%.

5-Benzyloxy-pyran-4(1H)-one-2-carboxylic acid (benzyl comenic acid) (13). Was synthesized according to a previous procedure.²⁴ Yield 74% ¹H NMR (300 MHz CDCl₃) δ 3.5 (s, 2H, benzyl- CH₂), 6.9 (s, 1H, CH₂), 7.4 (m, 5H, phenyl-H), 8.4 (s, 1H, pyrone-H).

NHS activation of 5-Benzyloxy-pyran-4(1H)-one-2-carboxylic acid (benzyl comenic acid). To a solution of (13) (300 mg 1.3 mmol) in dry THF (20 mL) was added NHS (150 mg 1.3 mmol). The reaction mixture was stirred for 30 minutes at room temperature under a N₂(g) atmosphere. DCC (268 mg 1.3 mmol) was added to the stirring solution and the mixture was continued to stir for 3 hours until TLC showed consumption of starting material. The DCU was filtered and the resulting filtrate was used in situ to synthesize CA1-3.

CA1P. To the above solution was added phenyl benzyl amine (238 mg 1.3 mmol) in THF (20 mL) dropwise. The reaction was stirred at room temperature over night under a N₂(g) atmosphere. The product precipitated as a white solid, which was filtered, washed with 20 mL methanol and dried to yield 375 mg. Yield 73% ¹H NMR (400 MHz d-DMSO) δ 4.5 (d, J=5.6 Hz, 2H, CH₂), 5.0 (s, 2H, benzyl- CH₂), 6.9 (s, 1H, pyrone-H), 7.4 (m, 10H, phenyl-H), 7.6 (m, 4H, phenyl-H), 8.3 (s, 1H, pyrone-H), 9.5 (t, J=12 Hz, 1H, amide-H). (+)-ESIMS: m/z 434.1 [M+Na]⁺.

CA1. To a suspension of CA1P (250 mg 0.63 mmol) in THF (130 mL) was added 25 mg of 10% Pd/C and placed under H₂ at 35 psi overnight at room temperature. The catalyst was filtered off and the filtrate was evaporated to an off-white solid, which was washed with 20 mL benzene and dried to yield 120 mg of a white solid. Yield 62% ¹H NMR (400 MHz d-DMSO) δ 4.5 (d, J=6.0 Hz, 2H, CH₂), 6.9 (s, 1H, pyrone-H), 7.4 (m, 5H, phenyl-H), 7.6 (m, 4H, phenyl-H), 8.1 (s, 1H, pyrone-H), 9.5 (t, J=12 Hz, 1H, amide-H), 9.6 (br s, 1H, OH). (−)-ESIMS: m/z 320.02

CA2P. The same general procedure was used as in the synthesis of CA1P with the exception that the reaction was heated to 65C overnight. Yield 84% $^1$H NMR (400 MHz d-DMSO) δ 5.0 (s, 2H, benzyl-CH$_2$), 7.0 (m, 5H, phenyl-H), 7.1 (t, J=21.6 Hz, 1H, phenyl-H), 7.4 (m, 7H, phenyl/pyrone-H), 7.8 (d, J=12.0 Hz, 2H, phenyl-H), 8.3 (s, 1H, pyrone-H), 10.7 (br, 1H, amide-H). (+)-ESIMS: m/z 436.05 [M+Na]$^+$.

CA3P. The same procedure was used as in the synthesis of CA2P. Yield 78% $^1$H NMR (400 MHz d-DMSO) δ 5.0 (s, 2H, benzyl- CH$_2$), 7.0 (s, 1H, pyrone-H), 7.4 (m, 8H, phenyl-H), 7.7 (t, 4H, J=15.0 Hz, phenyl-H), 7.8 (d, J=7.8 Hz, 2H, phenyl-H), 8.3 (s, 1H, pyrone-H), 10.7 (br, 1H, amide-H). (+)-APCIMS: m/z 398.02 [M$^+$+H].

CA3. The same procedure was used as in the synthesis of CA1 to yield a light yellow solid. Yield 43% $^1$H NMR (400 MHz d-DMSO) δ 7.0 (s, 1H, pyrone-H), 7.4 (br s, 1H, phenyl-H), 7.4 (t, J=15.2 Hz, 2H, phenyl-H), 7.7 (t, J=15.2 Hz, 4H, phenyl-H), 7.7 (d, J=8.8 Hz, 2H, phenyl-H), 8.2 (s, 1H, pyrone-H), 8.7 (br, 1H, amide-H), 10.7 (s, 1H, OH).

Scheme 3. Synthesis of CK1.

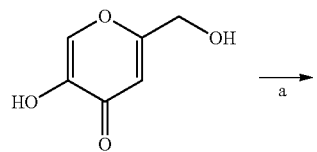

CK1 a) benzylamine, N(CH$_2$CH$_3$)$_3$, DMF, RT, 52%.

CK1. To a solution of chlorokojic acid (3 g 18.7 mmol) and benzylamine (2.25 mL 20.6 mmol) in DMF (15 mL) was added dropwise triethylamine (7.8 mL 56 mmol). The reaction mixture was stirred overnight at room temperature under a N$_2$(g) atmosphere. Water (60 mL) was added to the reaction mixture and the product was extracted with 3×200 mL CH$_2$Cl$_2$, dried with sodium sulfate, and filtered. The organic layer was evaporated to a dark yellow oil and purified by column chromatography on silica gel (elutant: 2-5% MeOH in CH$_2$Cl$_2$) to yield 2.2 g of a light yellow solid. Yield 52% $^1$H NMR (300 MHz d-DMSO) δ 2.5 (br m, 1H, NH), 3.5 (s, 2H, CH$_2$)), 3.7 (s, 2H, CH$_2$), 6.4 (s, 1H, pyrone-CH$_2$), 7.3 (m, 5H, phenyl-H), 8.0 (s, 1H, pyrone-H).

CK2. The same procedure was used as in the synthesis of CK1. Yield 26% $^1$H NMR (300 MHz CDCl$_3$) δ 2.8 (br quad, 4H, CH$_2$CH$_2$), 3.5 (s, 1H, NH)), 3.7 (s, 2H, CH$_2$), 6.4 (s, 1H, pyrone-H), 7.3 (m, 5H, phenyl-H), 7.9 (s, 1H, pyrone-H).

Scheme 4. Synthesis of KA1.

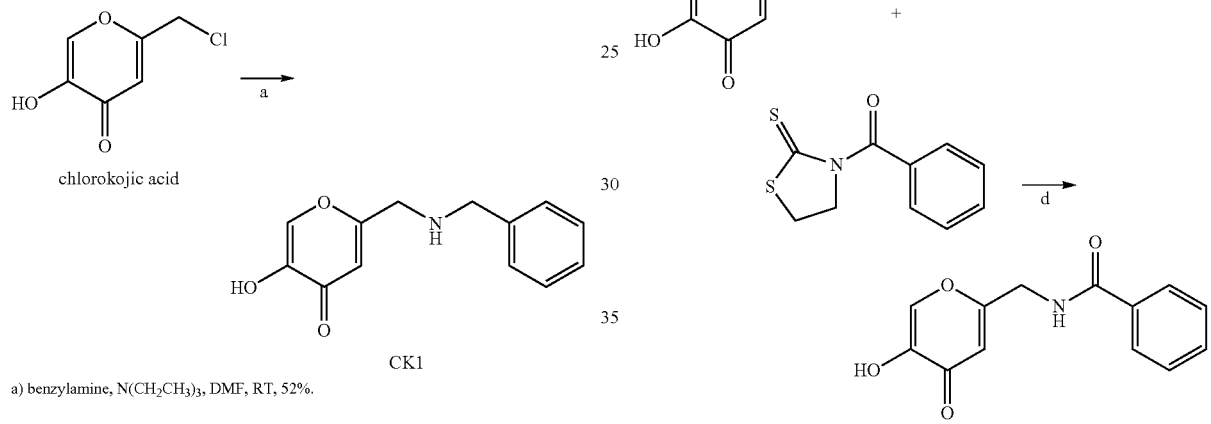

KA1 a) SOCl$_2$, dry CH$_2$Cl$_2$, RT, 88%; b) NaN$_3$, DMF, RT, 80%;
c) Lindlar Catalyst, H$_2$ 35 psi, MeOH, RT, 90%;
d) phenyl(2-thioxothiazolidin-3-yl)methanone, N(CH$_2$CH$_3$)$_3$, MeOH, RT, 51%.

Kojic Amine. Kojic Azide (325 mg 1.94 mol) was dissolved in 100 mL EtOH. To this solution was added Lindlar catalyst. The azide was hydrogenated at 35 psi for 1 hour at room temperature. Filtered off catalyst and rotovapped to light brown stolid. Dissolved in hot water and filtered off insolubles. Rotovapped filtrate to a white-tan solid 250 mg (91%). $^1$HNMR (DMSO-d$_6$, 400 MHz, 25° C.) δ3.52 (s, 2H, CH$_2$), 6.38 (s, 1H), 7.98 (s, 1H).IR (KBr): v1216, 1289, 1575, 1659 (C=0), 3374-2683 (b, NH$_3$, OH) cm$^{-1}$. MS ESI 142.1 (M+H), 140.0 (M–H).

General Procedure for MPIs KA1-4. Kojic amine (200 mg 1.4 mmol) was dissolved in methanol (60 mL). To this solution was added triethylamine (197.4 uL 1.4 mmol) and the corresponding activated amide (see above) dissolved in CH$_2$Cl$_2$. The solution was stirred overnight at room temperature under a N$_2$(g) atmosphere. The reaction mixture was evaporated to an oil which was purified by column chromatography on silica gel (elutant: 5-10% CH$_2$Cl$_2$/MeOH).

KA1. Yield 51% $^1$H NMR (400 MHz d-DMSO)δ 4.3 (d, J=5.4 Hz 2H, CH$_2$), 6.3 (s, 1H, pyrone-H), 7.5 (m, 3H, phenyl-H), 7.9 (d, J=6.9 Hz, 2H, phenyl-H), 8.0 (s, 1H, pyrone-H), 9.1 (t, J=12 Hz, 1H, amide-H).

KA2. The same procedure was used as in the synthesis of KA1. Yield 30% $^1$H NMR (400 MHz d-DMSO) δ3.5 (s, 2H, CH$_2$), 4.1 (d, J=5.4 Hz 2H, CH$_2$), 6.2 (s, 1H, pyrone-H), 7.3 (m, 5H, phenyl-H), 8.0 (s, 1H, pyrone-H), 8.5 (t, J=12 Hz, 1H, amide-H). $^{13}$CNMR (100 MHz, d-DMSO)δ 421, 110.3, 126.4, 128.2, 128.9, 135.8, 139.3, 145.5, 164.9, 170.4, 173.5.

KA3. The same procedure was used as in the synthesis of KA1. Yield 43% $^1$H NMR (400 MHz d-DMSO) δ2.5 (t, J=16 Hz, 2H, CH$_2$), 2.8 (t, J=15.6 Hz, 2H, CH$_2$), 4.1 (d, J=6.0 Hz 2H, CH$_2$), 6.2 (s, 1H, pyrone-H), 7.2 (m, 5H, phenyl-H), 8.0 (s, 1H, pyrone-H), 8.4 (t, J=12 Hz, 1H, amide-H), 9.1 (br s, 1H, pyrone-OH).

KA4. The same procedure was used as in the synthesis of KA1. Yield 70% $^1$H NMR (400 MHz d-DMSO) δ 1.8 (quintuplet, J=15.2 Hz 2H, CH$_2$)), 2.2 (t, J=16 Hz, 2H, CH$_2$), 2.6 (t, J=15.6 Hz, 2H, CH$_2$), 4.1 (d, J=6.0 Hz 2H, CH$_2$), 6.2 (s, 1H, pyrone-H), 7.2 (d, J=7.6 Hz, 2H, phenyl-H), 7.3 (t, J=15.2 Hz, 3H, phenyl-H), 8.0 (s, 1H, pyrone-H), 8.4 (t, J=12 Hz, 1H, amide-H), 9.1 (br s, 1H, pyrone-OH).

Scheme 5. Synthesis of HP32A, HP32B, AND HP32C.

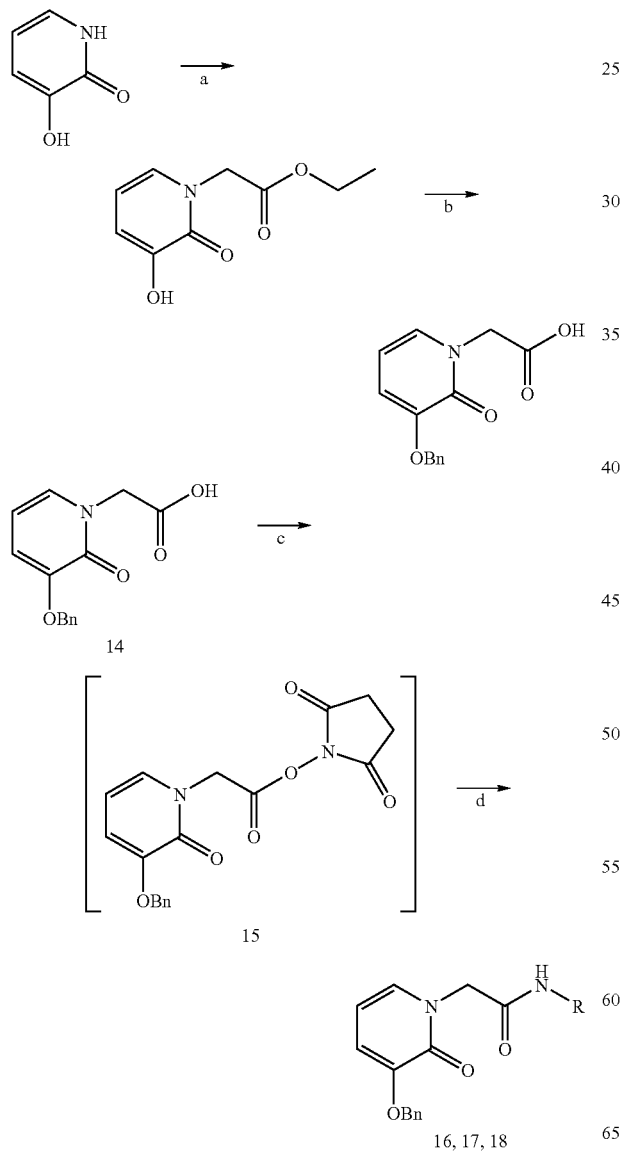

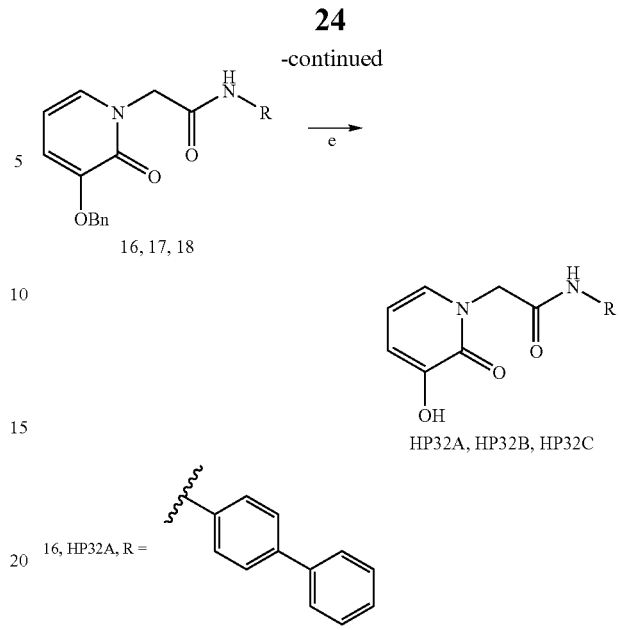

a) BrCH$_2$OEt, neat, 160° C., 40%; b) BnBr, NaOH, MeOH/H$_2$O, 95° C., 80%; c) DCC, NHS, DMF, 90%;
d) H$_2$NR, dry CH$_2$Cl$_2$, RT, 50%; e) Pd/C 10%, H$_2$(g) 35 psi, EtOH, RT, 40%.

3-(Benzyloxy)-1-[[(succinimidyloxy)carbonyl]methyl]-2-(1H)-pyridinone (15). To a stirring solution of 14$^{25}$ (0.95 g, 3.7 mmol) in 50 mL of dimethylformamide (DMF) were added solutions of N-hydroxysuccinimide (NHS, 0.44 g, 3.9 mmol) and dicyclohexylcarbodiimide (DCCI, 0.80 g, 3.9 mmol) each by dropwise addition and each in DMF (5 mL). The reaction mixture was protected from light with aluminum foil and stirred under a dinitrogen atmosphere at RT overnight. Glacial acetic acid (100 µL) was added. After stirring the mixture for 1 h, a white crystalline cubic salt, which should be a salt of N,N'-dicyclohexylurea (DCU), was removed by vacuum filtration. The solvent was removed by rotary evaporation to yield the crude product. Recrystallization from ethyl acetate (EtOAc) and isolation by vacuum filtration gave the pure product as white crystalline needles. Another batch of product was isolated by concentrating the EtOAc filtrate followed by cooling the mixture to 0° C. overnight and isolating the crystals by vacuum filtration the following day. Yield: 88%. $^1$H NMR (d$^6$-DMSO, 400 MHz, 25° C.): δ 2.80 (s, 4H, succinimidyl-H), 5.02 (s, 2H, —CH$_2$—), 5.17 (s, 2H, —CH$_2$—), 6.20 (t, J=7.2 Hz, 1H, Ar—H), 6.95 (d, J=7.6 Hz, 1H, Ar—H), 7.39 (m, 6H, Ar—H, benzyl-H).

3-Benzyloxy-1-[(biphenylcarbamoyl)methyl]-2-(1H)-pyridinone (16). 15 (0.5 g, 1.4 mmol) was dissolved in 40 mL of CH$_2$Cl$_2$. 4-aminobiphenyl (0.26 g, 1.5 mmol) was dissolved in 10 mL of CH$_2$Cl$_2$ to yield a chocolate brown solution and was quickly added to the stirring solution of 15. The reaction flask was protected from light with aluminum foil and stirred at room temperature under a dinitrogen atmosphere for 22 h. A white solid was removed by vacuum filtration. The $CH_2Cl_2$ filtrate layer was washed with 0.05 M aqueous sodium bicarbonate solution (3×25 mL). The methylene chloride layer was washed with dd$H_2O$ (1×25 mL) and then dried over anhydrous sodium sulfate. The clear, colorless solution was concentrated by rotary evaporation to yield a white solid. Yield: 51%. NMR (d$^6$-DMSO, 400 MHz, 25° C.): δ 4.77 (s, 2H, —$CH_2$—), 5.02 (s, 2H, —$CH_2$—), 6.16 (t, J=7.0 Hz, 1H, Ar—H), 6.94 (d, J=5.6 Hz, 1H, Ar—H), 7.39 (m, 9H, Biphenyl-H), 7.64 (m, 6H, Ar—H, Bz-H), 10.43 (d, J=6.9 Hz, 1H, —NH—). ESI-MS: m/z 433.1 [M+Na]$^+$, m/z 411.0 [M+H]$^+$.

3-Hydroxy-1-[biphenylcarbamoyl)methyl]-2-(1H)-pyridinone (HP32A). 16 (200 mg, 0.5 mmol) was suspended in 100 mL of EtOH. 10% (w/w, 38 mg) of 10% Pd/C catalyst was added to the hydrogenation flask (500 mL Pyrex® Parr reaction bottle tested to 120 psi, max. working pressure of 60 psi). The Parr hydrogenation system located in the VanNieuwenhze lab was used for the deprotection reactions. The hydrogen pressure was set to 35 psi with agitation, and the process went on for 10 h. A white precipitate was present even after the reaction was stopped, but this white product reacted with iron(III) to give a pink product instead of no reaction as with the protected starting material. The catalyst was removed by vacuum filtration and separated from the product by dissolving the white precipitate in 125 mL hot $CH_2Cl_2$ and MeOH. The clear solution was concentrated by rotary evaporation to yield a white solid. The solid was washed with MeOH to remove residual DCU and recrystallized from EtOH to yield a white, feathery microcrystalline solid. Yield: 31%. $^1$H NMR (d$^6$-DMSO, 400 MHz, 25° C.): δ 4.79 (s, 2H, —$CH_2$—), 6.12 (t, J=7.2 Hz, 1H, Ar—H), 6.73 (d, J=7.2 Hz, 1H, Ar—H), 7.15 (d, J=6.8 Hz, 1H, Ar—H), 7.31 (t, J=7.2 Hz, 1H, Biphenyl-H), 7.42 (t, J=7.0 Hz, 2H, Biphenyl-H), 7.64 (m, 6H, Biphenyl-H), 9.07 (s, 1H, —OH), 10.45 (s, 1H, —NH—). ESI-MS: m/z 320.9 [M+H]$^+$, m/z 319.1 [M–H]$^-$. Anal. Calcd for $C_{19}H_{16}N_2O_3 \cdot 1/2H_2O$: C, 69.29; H, 5.20; N, 8.51. Found: C, 68.96; H, 5.60; N, 8.34.

3-Benzyloxy-1-[(phenoxycarbamoyl)methyl]-2-(1H)-pyridinone (17). 15 (1.0 g, 2.8 mmol) was dissolved in 100 mL of dry $CH_2Cl_2$. 4-phenoxyaniline (0.57 g, 3.1 mmol) was dissolved in 10 mL of $CH_2Cl_2$ to yield a clear, brown solution and was quickly added to the stirring solution of 15. The reaction flask was protected from light with aluminum foil and stirred at room temperature under a dinitrogen atmosphere for 21 h. The resultant clear, light brown $CH_2Cl_2$ solution was washed with 0.05 M aqueous sodium bicarbonate solution (3×50 mL). The methylene chloride layer was washed with dd$H_2O$ (1×50 mL) and then dried over anhydrous sodium sulfate. The clear, colorless solution was concentrated by rotary evaporation to yield a white solid. Yield: 55%. $^1$H NMR (d$^6$-DMSO, 300 MHz, 25° C.): δ 4.73 (s, 2H, —$CH_2$—), 5.01 (s, 2H, —$CH_2$—), 6.15 (t, J=7.2 Hz, 1H, Ar—H), 7.35 (m, 16H, 2 Ar—H, Bz-H, Phenoxy-H), 10.36 (s, 1H, —NH—).

3-Hydroxy-1-[(phenoxycarbamoyl)methyl]-2-(1H)-pyridinone (HP32B). 17 (350 mg, 0.8 mmol) was suspended in 175 mL of EtOH. 10% (w/w, 38 mg) of 10% Pd/C catalyst was added to the hydrogenation flask (500 mL Pyrex® Parr reaction bottle tested to 120 psi, max. working pressure of 60 psi). The Parr hydrogenation system located in the VanNieuwenhze lab was used for the deprotection reactions. The hydrogen pressure was set to 35 psi with agitation, and the process went on for 41 h. A white precipitate was present even after the reaction was stopped, but this white product reacted with iron(III) to give a reddish product instead of no reaction as seen with the protected starting material. The catalyst was removed by vacuum filtration and separated from the product by dissolving the white precipitate in 125 mL hot $CH_2Cl_2$ and MeOH and THF. The clear solution was concentrated by rotary evaporation to yield a white solid. The solid was washed with MeOH to remove residual DCU to yield a white, feathery microcrystalline solid. Yield: 57%. $^1$H NMR (d$^6$-DMSO, 400 MHz, 25° C.): δ 4.75 (s, 2H, —$CH_2$—), 6.11 (t, J=7.0 Hz, 1H, Ar—H), 6.72 (d, J=7.2 Hz, 1H, Ar—H), 6.97 (m, 4H, Phenoxy-H), 7.11 (m, 2H, Ar—H, Phenoxy-H), 7.36 (t, J=7.2 Hz, 2H, Phenoxy-H), 7.58 (d, J=6.8 Hz, 2H, Phenoxy-H), 9.03 (s, 1H, —OH), 10.36 (s, 1H, —NH—). APCI-MS: m/z 336.9 [M+H]$^+$. Anal. Calcd for $C_{19}H_{16}N_2O_4$: C, 67.85; H, 4.79; N, 8.33. Found: C, 67.75; H, 5.07; N, 8.49.

3-Benzyloxy-1-[(phenylbenzylcarbamoyl)methyl]-2-(1H)-pyridinone (18). 15 (0.5 g, 1.4 mmol) was dissolved in 50 mL of dry $CH_2Cl_2$. 4-phenylbenzylamine (0.28 g, 1.5 mmol) was dissolved in 10 mL of dry $CH_2Cl_2$ to yield an almost clear, colorless solution and was quickly added to the stirring solution of 15. The reaction flask was protected from light with aluminum foil and stirred at room temperature under a dinitrogen atmosphere for 18 h. A white solid was removed by vacuum filtration. A second crop of white precipitate was isolated after cooling the filtrate at 4° C. for 3 h. The $CH_2Cl_2$ filtrate layer was washed with 0.05 M aqueous sodium bicarbonate solution (3×25 mL). The methylene chloride layer was washed with dd$H_2O$ (1×25 mL) and then dried over anhydrous sodium sulfate. The clear, colorless solution was concentrated by rotary evaporation to yield a white solid. Yield: 55%. $^1$H NMR (d$^6$-DMSO, 400 MHz, 25° C.): δ 4.33 (d, J=6.0 Hz, 2H, —$CH_2$—), 4.61 (s, 2H, —$CH_2$—), 5.00 (s, 2H, —$CH_2$—), 6.12 (t, J=7.2 Hz, 1H, Ar—H), 6.91 (d, J=7.6 Hz, 1H, Ar—H), 7.22 (d, J=6.8 Hz, 1H, Ar—H), 7.39 (m, 9H, Phenyl-H, Bz-H), 7.62 (m, 5H, Bz-H), 8.70 (t, J=5.8 Hz, 1H, —NH—).

3-Hydroxy-1-[(phenylbenzylcarbamoyl)methyl]-2-(1H)-pyridinone (HP32C). 18 (280 mg, 0.7 mmol) was suspended in 150 mL of EtOH. 10% (w/w, 38 mg) of 10% Pd/C catalyst was added to the hydrogenation flask (500 mL Pyrex® Parr reaction bottle tested to 120 psi, max. working pressure of 60 psi). The Parr hydrogenation system located in the VanNieuwenhze lab was used for the deprotection reactions. The hydrogen pressure was set to 35 psi with agitation, and the process went on for 19 h. A white precipitate was present even after the reaction was stopped, but this white product reacted with iron(III) to give a pink product instead of no reaction as with the protected starting material. The catalyst was removed by vacuum filtration and separated from the product by dissolving the white precipitate in 100 mL hot $CH_2Cl_2$. An additional batch of product was isolated by cooling the EtOH filtrate to 0° C. for 2 h. The clear solution was concentrated by rotary evaporation to yield a white solid. The solid was washed with MeOH to remove residual DCU. Yield: 22%. $^1$H NMR (d$^6$-DMSO, 400 MHz, 25° C.): δ 4.34 (d, J=6.0 Hz, 2H, —$CH_2$—), 4.63 (s, 2H, —$CH_2$—), 6.08 (t, J=7.2 Hz, 1H, Ar—H), 6.69 (d, J=7.2 Hz, 1H, Ar—H), 7.10 (d, J=6.4 Hz, 1H, Ar—H), 7.44 (m, 5H, Bz-H), 7.64 (m, 4H, Phenyl-H), 8.70 (t, J=5.6 Hz, 1H, —NH—), 9.02 (s, 1H, —OH). APCI-MS: m/z 334.9 [M+H]$^+$. Anal. Calcd for $C_{20}H_{18}N_2O_3$: C, 71.84; H, 5.43; N, 8.38. Found: C, 71.49; H, 5.78; N, 8.52.

The following derivatives were prepared similarly:
CA1
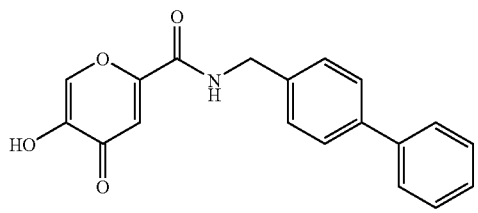
CA2
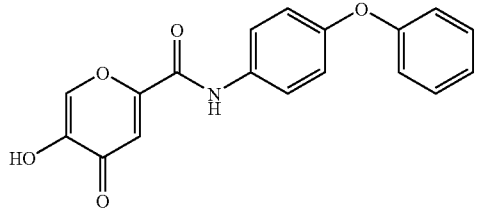
CA3
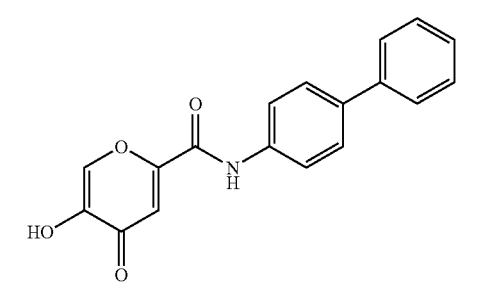
CK1
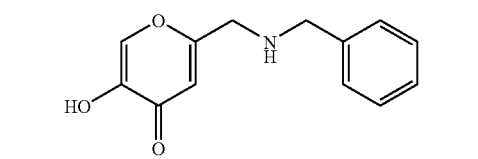
CK2
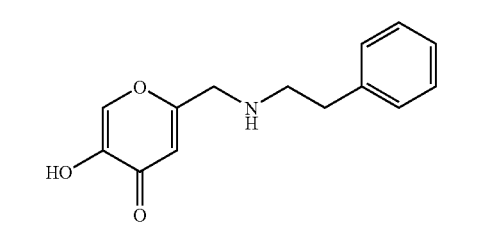
CK3
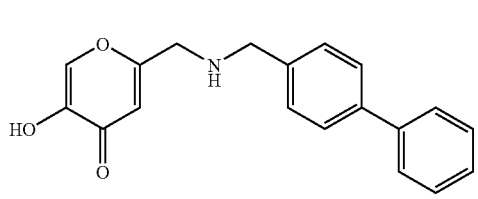
AM1
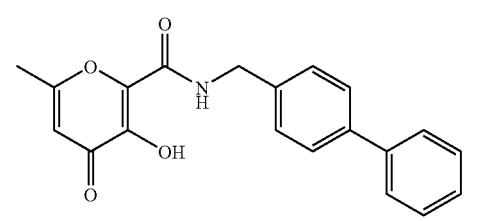
-continued
AM2
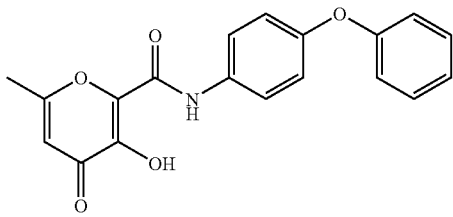
AM3
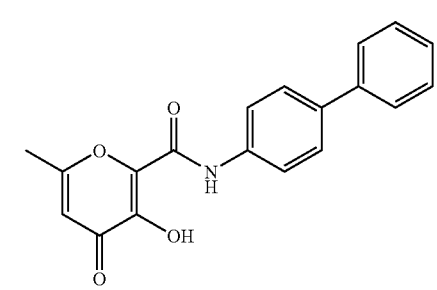
KA1
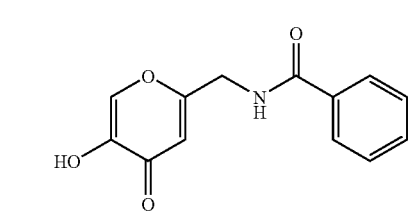
KA2
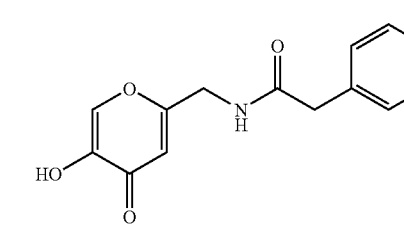
KA3
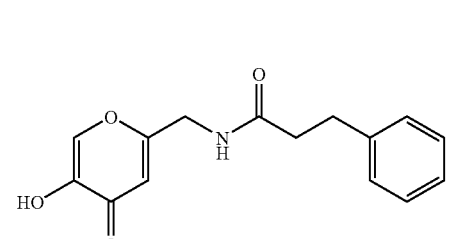
TKA3
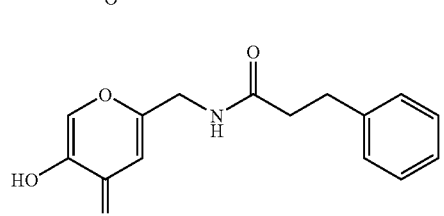
KA4
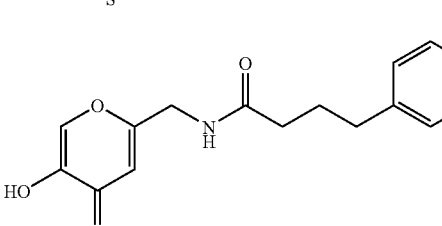

-continued

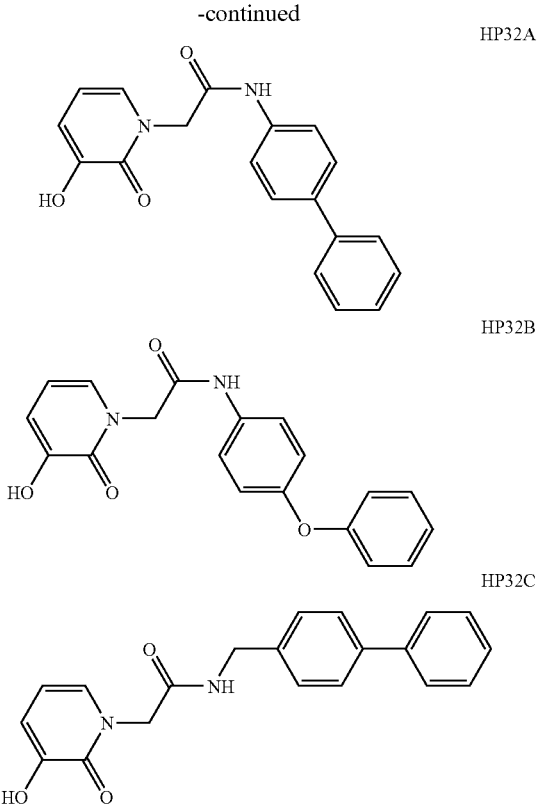

It may be desirable optionally to use a protecting group during all or portions of the above described synthetic procedures. Such protecting groups and methods for their introduction and removal are well known in the art. See Greene, T. W.; Wutz, P. G. M. "Protecting Groups In Organic Synthesis" second edition, 1991, New York, John Wiley & Sons, Inc.

Computer Modeling Analysis. Computer modeling was utilized to facilitate the design of the full-length MMPi described above. This was performed as per a published procedure[26] and further augmented with the use of LUDI (Accelyrs, Inc.).

Oxygen-Containing MPIs. Since MMPs were first linked to diseases such as inflammatory conditions such as arthritis and cancer, hydroxamate-derived drugs have been the staple for MMPi design.[1] There has been much effort placed to improve the design of better peptidomimetic "backbones" of MMP inhibitors, with the effort focused on enhancing the ZBG being relatively miniscule in comparison. Furthermore, many HDACi and LFi compounds are also based on the hydroxamate ZBG.

New chelators were selected that were expected to bind as well as or better than hydroxamates. Hydroxypyridinones (HOPOs) were selected as lead compounds for several reasons. HOPOs are known to be strong metal chelators.[27,28] In addition, the cyclic structure of hydroxypyridinones reduces the degrees of freedom in the ligand, preventing the cis to trans isomerization that can occur in hydroxamic acids, which ultimately detracts from the thermodynamic affinity of the metal-ligand interaction. The basicity of hydroxypyridinones varies between isomers, which potentially allows for tuning the protonation state of the ligand to accommodate possible hydrogen-bonding interactions in the protein active site.[29] Finally, many hydroxypyridinones and related compounds have been or are used in medical and food industry applications,[30] suggesting a reasonable level of biological tolerance for these chemical moieties. Several hydroxypyridinone and hydroxypyrone derivatives were also developed, including N-methylated hydroxypyridinones, a hydroxypyridinethione, and 3-hydroxy-2-methyl-4-pyrone (see above and also see FIG. 1).

Sulfur-Containing MPIs. Sulfur-containing ligands may be very good ZBGs because of the apparent thiophilicity of zinc(II).[31,32] Similarly, other thiol-based MPIs have been studied and have shown reasonably good activity when compared to hydroxamate-based inhibitors.[1,16,33,34] Combining the best features of both hydroxamates and thiol inhibitors into a single ZBG, sulfur-containing ZBGs were developed because of the higher affinity of sulfur for the $Zn^{2+}$ ion compared to oxygen. Furthermore, ZBGs with rigid ring structures that lock the O,S-donor atoms in a cis conformation, can bind $Zn^{2+}$ ion in a bidentate fashion, to minimize oxidation and disulfide bond formation, which can be problems for thiol MPI, in biological systems. FIG. 1 discloses the sulfur-containing molecules which were evaluated as ZBGs for MPI.

Figure 3:
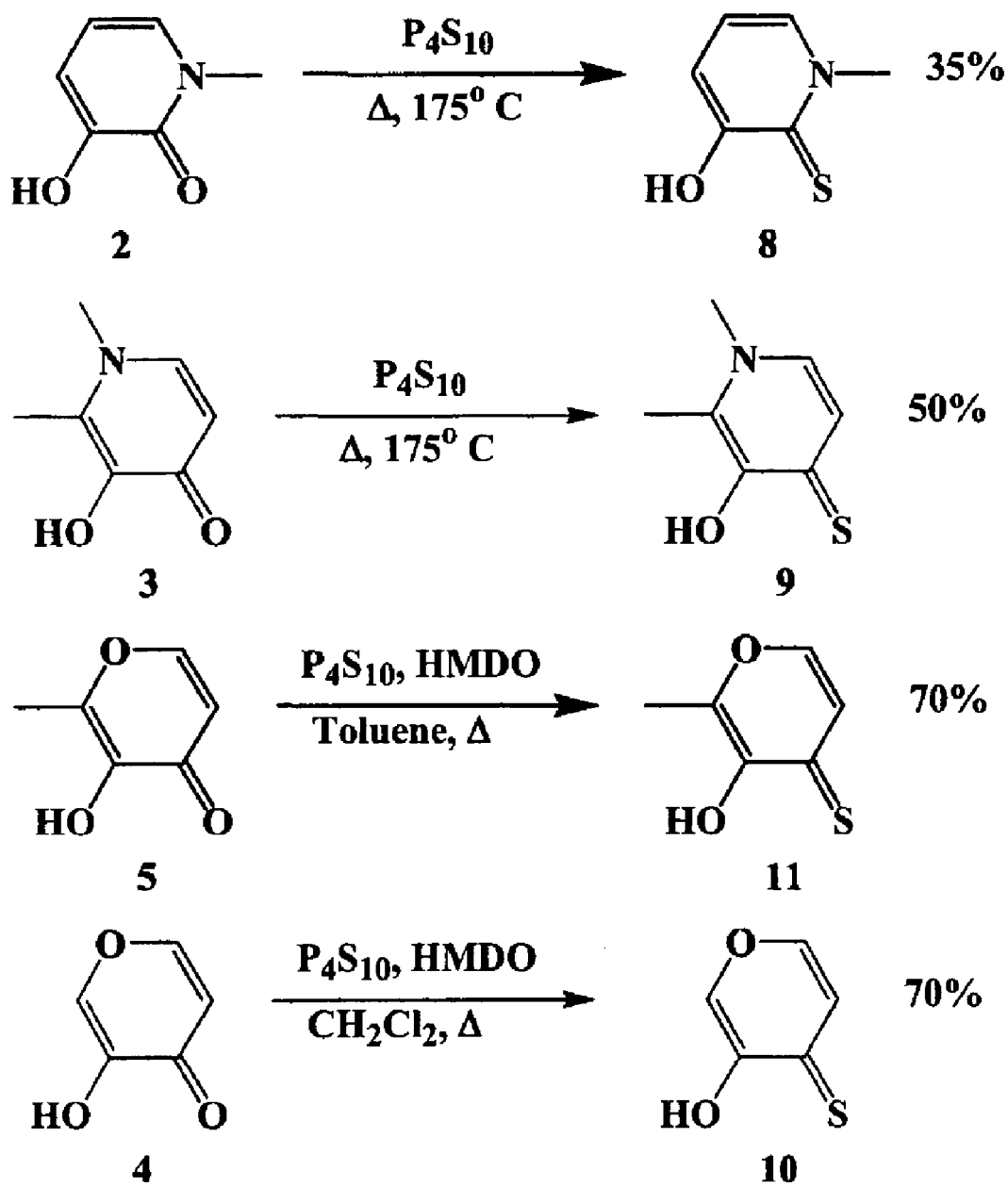
FIG. 3. Syntheses of representative O,S novel ZBGs. From top to bottom, synthesis of Me3,2-HOPTO (8) from Me3,2-1-HOPTO (2), 3,4-HOPTO (9) from commercially available 3,4-HOPO (3), thiopyromeconic acid (10) from pyromeconic acid (4), and thiomaltol (11) from commercially available maltol (5).

Various thionation routes were explored to optimize reaction conditions. Facile, high-yielding reactions for novel sulfur-containing ligands have been developed (FIG. 3).[35,36] As demonstrated above for oxygen-containing ZBGs, the sulfur-containing ZBGs 11, 8, and 9 bind the $Zn^{2+}$ metal center in $(Tp^{Ph,Me})Zn$ in a bidentate fashion similar to acetohydroxamic acid, which makes them especially promising ZBGs.

MMP Assays with ZBGs of the Present Invention. Biological assays were used to test the potency of the ZBGs with respect to binding the MMP enzyme.[37] The assay plate was incubated with buffer, various concentrations of ZBG, and enzyme MMP-3 at 37° C. for 1 h. Increasing fluorescence was measured over time at 37° C.

As shown on the Table on FIG. 4, all of the ZBGs tested in the biological assay were more potent than acetohydroxamic acid (AHA). The O,S mixed donor ligands (7-11) were all about two orders of magnitude more potent than AHA. The raw data from the assays (FIG. 5) were converted to percentages of the control activity (FIG. 6) by comparing the slopes of the data sets to the control slope. Control activity was determined from wells with enzyme, buffer, and substrate. The amount of fluorescence over time correlated with MMP-3 enzymatic activity, wherein, more fluorescence over shorter time periods indicated a less potent ZBG. The $IC_{50}$ values were determine by a linear fit as per the assay kit instructions (Biomol, Inc.). In order to confirm the values obtained fluorescence-based assays, additional experiments were performed on some ZBGs using a widely-used colorimetric-based assay.[38] The $IC_{50}$ values from the colorimetric assays (FIG. 4) are in good agreement with those obtained by fluorescence measurements.

Based on the promising results obtained for the compounds in FIG. 1, the $IC_{50}$ value for inhibitors comprising at least one organic substituent were measured. For AM1 the $IC_{50}$ value was 240 nM for MMP-3. AM1 inhibited MMP-1 at an $IC_{50}$ value >50000 nM and inhibited MMP-2 at an $IC_{50}$ value of 9300 nM. Additional representative $IC_{50}$ values for MMP-3 inhibition include AM3: 90 µM; KA2: 200 µM; KA3: 930 µM; TKA3: 90 µM; KA4: 400 µM; and CA1: 25% inhibition @ 50 µM.

The design of potent and selective metalloprotein inhibitors such as matrix metalloproteinase inhibitors presents the possibility to treat many diseases, including those disclosed in Refs. 1-3, incorporated by reference herein. The ZBGs shown in FIG. 1 can readily be elaborated by adding a wide variety of substituents to the open ring positions, particularly peptidomimetic backbones, such as those shown in Reference 1 and in EPA 126,974.

REFERENCES (1) Whittaker, M.; Floyd, C. D.; Brown, P.; Gearing, A. J. H. *Chem. Rev.* 1999, 99, 2735-2776.
(2) Overall, C. M.; Lüpez-Otin, C. *Nat. Rev. Cancer* 2002, 2, 657-672.
(3) Puerta, D. T.; Cohen, A. *Curr. Top. Med. Chem.* 2004, 4, 1551-1573.
(4) Wegener, D.; Hildmann, C.; Schwienhorst, A. *Mal. Genet. Metab.* 2003, 80, 138-147.
(5) Grozinger, C. M.; Schreiber, S. L. *Chem. Biol.* 2002, 9, 3-16.
(6) Vigushin, D. M.; Coombes, R. C. *Anti-Cancer Drugs* 2002, 13, 1-13.
(7) Miller, T. A.; Witter, D. J.; Belvedere, S. *J. Med. Chem.* 2003, 46, 5098-5116.
(8) Johnstone, R. W. *Nat. Rev. Drug. Discov.* 2002, 1, 287-299.
(9) Park, J. M.; Greten, F. R.; Li, Z.-W.; Karin, M. *Science* 2002, 297, 2048-2051.
(10) Collier, R. J.; Young, J. A. T. *Anu. Rev. Cell Dev. Biol.* 2003, 19, 45-70.
(11) Pezard, C.; Berche, P.; Mock, M. *Infect. Immun.* 1991, 59, 3472-3477.
(12) Panchal, R. G.; Hermone, A. R.; Nguyen, T. L.; Wong, T. Y.; Schwarzenbacher, R.; Schmidt, J.; Lane, D.; McGrath, C.; Turk, B. E.; Burnett, J.; Aman, M. J.; Little, S.; Sausville, E. A.; Zaharevitz, D. W.; Cantley, L. C.; Liddington, R. C.; Gussio, R.; Bavari, S. *Nat. Struct. Mol. Biol,* 2004, 11, 67-72.
(13) Turk, B. E.; Wong, T. Y.; Schwarzenbacher, R.; Jarrell, E. T.; Leppla, S. H.; Collier, R. J.; Liddington, R. C.; Cantley, L. C. *Nature* 2004, 11, 60-66.
(14) Lee, L. V.; Bower, K. E.; Liang, F.-S.; Shi, J.; Wu, D.; Sucheck, S. J.; Vogt, P. K.; Wong, C.-H. *J. Am. Chem. Soc.* 2004, 126, 4774-4775.
(15) Agrawal, A.; Pulendran, B. *Cell. Mol. Life Sci.* 2004, 61, 2859-2865.
(16) Puerta, D. T.; Cohen, S. M. *Inorg. Chem.* 2002, 41, 5075-5082.
(17) Puerta, D. T.; Cohen, S. M. *Inorg. Chem.* 2003, 42, 3423-3430.
(18) Parkin, G. *Chem. Commun.* 2000, 20.
(19) Trofimenko, S. *Chem. Rev.* 1993, 93, 943-980.
(20) Vahrenkamp, H. *Acc. Chem. Res.* 1999, 32, 589-596.
(21) Ruf, M.; Weis, K.; Brasack, I.; Vahrenkamp, H. *Inorg. Chim. Acta* 1996, 250, 271-281.
(22) Puerta, D. T.; Lewis, J. A.; Cohen, S. M. *J. Am. Chem. Soc.* 2004, 126, 8388-8389.
(23) Liu, Z. D.; Piyamongkol, S.; Liu, D. Y.; Khodr, H. H.; Lu, S. L.; Hider, R. C. *Bioorg. Med. Chem.* 2001, 9, 563-573.
(24) Aytemir, M. D.; Hider, R. C.; Erol, D. D.; Ekizoglu, M. O. M. *Turk. J. Chem.* 2003, 27, 445-452.
(25) Streater, M.; Taylor, P. D.; Hider, R. C.; Porter, J. *J. Med. Chem.* 1990, 33, 1749-1755.
(26) Puerta, D. T.; Schames, J. R.; Henchman, R. H.; McCammon, J. A.; Cohen, S. M. *Angew. Chem. Int. Ed.* 2003, 42, 3772-3774.
(27) Abu-Dari, K.; Karpishin, T. B.; Raymond, K. N. *Inorg. Chem.* 1993, 32, 3052-3055.
(28) Scarrow, R. C.; Riley, P. E.; Abu-Dari, K.; White, D. L.; Raymond, K. N. *Inorg. Chem.* 1985, 24, 954-967.
(29) Babine, R. E.; Bender, S. L. *Chem. Rev.* 1997, 97, 1359-1472.
(30) Thompson, K. H.; Orvig, C. In *Metal Ions in Biological Systems*; Sigel, A., Sigel, H., Eds.; Marcel Dekker, Inc.: New York, 2004; Vol. 41, pp 221-253.
(31) Lippard, S. J.; Berg, J. M. *Principles of Bioinorganic Chemistry*; University Science Books: Mill Valley, 1994.
(32) Sigel, H.; McCormick, D. B. *Chem. Rev.* 1970, 3, 201-208.
(33) Levin, J. I.; DiJoseph, J. F.; Killar, L. M.; Sharr, M. A.; Skotnicki, J. S.; Patel, D. V.; Xiao, X.-Y.; Shi, L.; Navre, M.; Campbell, D. A. *Bioorg. Med. Chem. Lett.* 1998, 8, 1163-1168.
(34) Campbell, D. A.; Xiao, X.-Y.; Harris, D.; Ida, S.; Mortezaei, R.; Ngu, K.; Shi, L.; Tien, D.; Wang, Y.; Navre, M.; Patel, D. V.; Sharr, M. A.; DiJoseph, J. F.; Killar, L. M.; Leone, C. L.; Levin, J. I.; Skotnicki, J. S. *Bioorg. Med. Chem. Lett.* 1998, 8, 1157-1162.
(35) Lewis, J. A.; Puerta, D. T.; Cohen, S. M. *Inorg. Chem.* 2003, 42, 7455-7459.
(36) Lewis, J. A.; Cohen, S. M. *Inorg. Chem.* 2004, 43, 6534-6536.
(37) Knight, C. G.; Willenbrock, F.; Murphy, G. *FEBS Lett* 1992, 296, 263-266.
(38) Weingarten, H.; Martin, R.; Feder, J. *Biochemistry* 1985, 24, 6730-6734.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method of inhibiting metalloprotein activity in a mammal or of treating a mammal in need of therapy for a pathology, condition, or symptom associated with metalloprotein activity, which comprises administering to the mammal an effective amount of a compound of formula

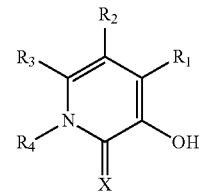

wherein X is O, and wherein $R^1$, $R^2$, and $R^3$ is each hydrogen, and wherein $R^4$ is biphenylcarbamyl- $(C_1)$alkyl, biphenyl$(C_1$-$C_6)$alkylcarbamyl, $(C_1)$alkyl, or phenoxyphenylcarbamyl $(C_1)$alkyl, or a pharmaceutically-acceptable salt thereof.

2. The method of claim 1 wherein the compound is administered as a composition comprising a pharmaceutically acceptable excipient.

3. The method of claim 1 wherein the compound is administered orally.

4. The method of claim 1 wherein the compound is administered parenterally.

5. The method of claim 1 wherein the pathology comprises MMP activity, or histone deacetylase activity, or anthrax lethal factor activity.

6. The method of claim 1 wherein the pathology comprises cancer, or inflammation, or myocardial infarction.

* * * * *

UNITED STATES PATENT AND TRADEMARK OFFICE
CERTIFICATE OF CORRECTION

PATENT NO.        : 8,008,510 B2
APPLICATION NO.   : 12/722623
DATED             : August 30, 2011
INVENTOR(S)       : David T. Puerta et al.

Page 1 of 4

It is certified that error appears in the above-identified patent and that said Letters Patent is hereby corrected as shown below:

On page 2, under "Other Publications", in column 1, line 23, delete "Applicatiion" and insert -- Application --, therefor.

On page 2, under "Other Publications", in column 1, line 25, delete "Applicatiion" and insert -- Application --, therefor.

On page 2, under "Other Publications", in column 1, line 31, delete "Serical" and insert -- Serial --, therefor.

On page 2, under "Other Publications", in column 2, line 28, delete "Medicial" and insert -- Medical --, therefor.

On page 2, under "Other Publications", in column 2, line 44-45, delete "Mettaloproteinase" and insert -- Metalloproteinase --, therefor.

On page 3, under "Other Publications", in column 2, line 1, delete "Futoenone" and insert -- Fluorenone --, therefor.

On page 3, under "Other Publications", in column 2, line 2, delete "Biorganic" and insert -- Bioorganic --, therefor.

On page 3, under "Other Publications", in column 2, line 11, delete "Anthax Lethan" and insert -- Anthrax Lethal --, therefor.

On Sheet 4 of 6, Row 3, column 5, Figure 4, line 1, delete "1500((±10)" and insert -- 1500(±10) --, therefor.

In column 2, line 27, delete "animoglycosides," and insert -- aminoglycosides, --, therefor.

Signed and Sealed this
Twenty-ninth Day of November, 2011

David J. Kappos
*Director of the United States Patent and Trademark Office*

CERTIFICATE OF CORRECTION (continued)

In column 4, lines 37-38, delete "Me3,2-1-HOPTO and insert -- Me3,2-HOPO --, therefor.

In column 4, line 50, after "minutes" insert -- . --.

In column 5, line 39, delete "nucelosomes" and insert -- nucleosomes --, therefor.

In column 5, line 55, delete "sirutins." and insert -- sirtuins. --, therefor.

In column 6, lines 26-27, delete "($C_3$-$C_6$)cycloalkyl($C_1$-$C_6$)alkyl)," and insert -- ($C_3$-$C_6$)cycloalkyl(($C_1$-$C_6$)alkyl), --, therefor.

In column 7, line 10, after " 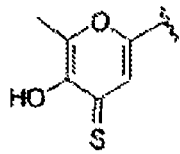 " insert -- . --.

In column 7, line 23, delete "biphenyl oxy" and insert -- biphenyloxy --, therefor.

In column 7, line 28, delete "phenoxyphenylcarbarnyl," and insert -- phenoxyphenylcarbamyl, --, therefor.

In column 7, line 32, delete "phenoxyphenylearbamylmethyl," and insert -- phenoxyphenylcarbamylmethyl, --, therefor.

In column 7, line 35, delete "$R^1$," and insert -- $R^1$. --, therefor.

In column 8, line 27, delete "at" and insert -- al. --, therefor.

In column 9, line 16, delete "-hydroxypropyl," and insert -- 1-hydroxypropyl, --, therefor.

In column 9, line 65, delete "[ZBG" and insert -- [ZBG] --, therefor.

In column 10, line 43, delete "N,N-dibenzylethylenediamine," and insert -- N,N'-dibenzylethylenediamine, --, therefor.

In column 10, line 54, delete "algesic," and insert -- algenic, --, therefor.

In column 11, line 6, delete "dilutent" and Insert -- diluent --, therefor.

In column 13, line 61, delete "polaxomers," and insert-- poloxamers, --, therefor.

In column 14, line 14, after "such" insert -- as --.

In column 15, line 19, delete "50 ng" and insert -- 50 ng, --, therefor.

CERTIFICATE OF CORRECTION (continued)
U.S. Pat. No. 8,008,510 B2

In column 19, line 7, delete "Hz 2H," and insert -- Hz, 2H, --, therefor.

In column 19, line 8, delete "Hz 2H," and insert -- Hz, 2H, --, therefor.

In column 19, line 17, delete "NMR." and insert -- NMR --, therefor.

In column 19, line 18, delete "Hz 1H," and insert -- Hz, 1H, --, therefor.

In column 20, line 67, after "320.02" insert -- [M⁻-H]. --, therefor.

In column 21, line 49, delete "(elutant:" and insert -- (eluent: --, therefor.

In column 21, line 52, delete "CH$_2$))," and insert -- CH$_2$), --, therefor.

In column 21, line 56, delete "NH))," and insert -- NH), --, therefor.

In column 22, line 45, delete "1.94 mol)" and insert -- 1.94 mmol) --, therefor.

In column 22, line 50, delete "$^1$HNMR" and insert -- $^1$H NMR --, therefor.

In column 22, line 50, delete "δ3.52" and insert -- δ 3.52 --, therefor.

In column 22, line 81, delete "(elutant:" and insert -- (eluent: --, therefor.

In column 22, line 62, delete "d-DMSO)δ" and insert -- d-DMSO) δ --, therefor.

In column 22, line 67, delete "δ3.5" and insert -- δ 3.5 --, therefor.

In column 23, line 3, delete "d-DMSO)δ" and insert -- d-DMSO) δ --, therefor.

In column 23, line 7, delete "δ2.5" and insert --δ 2.5--, therefor.

In column 23, line 14, delete "CH$_2$))," and insert -- CH$_2$), --, therefor.

In column 23, line 15, delete "Hz 2H," and insert -- Hz, 2H, --, therefor.

In column 25, line 10, delete "51%. NMR" and insert -- 51%. $^1$H NMR --, therefor.

In column 25, line 15, delete "[biphenylcarbamoyl)methyl]" and
insert -- [(biphenylcarbamoyl)methyl] --, therefor.

In column 29, lines 42-43, delete "(Accelyrs, Inc.)." and insert -- (Accelrys, Inc.). --, therefor.

In column 31, line 13, delete "Mal." and insert -- Mol. --, therefor.

In column 31, line 33, delete "Biol," and insert -- Biol. --, therefor.